US006312835B1

(12) United States Patent
Wang et al.

(10) Patent No.: US 6,312,835 B1
(45) Date of Patent: Nov. 6, 2001

(54) LUMINESCENT COMPOUNDS AND METHODS OF MAKING AND USING SAME

(75) Inventors: Suning Wang, Kingston; Wang Liu, North York; Abdi Hassan, Windsor, all of (CA)

(73) Assignee: Queen's University at Kingston, Kingston (CA)

( * ) Notice: Subject to any disclaimer, the term of this patent is extended or adjusted under 35 U.S.C. 154(b) by 0 days.

(21) Appl. No.: 09/022,416

(22) Filed: Feb. 12, 1998

Related U.S. Application Data

(60) Provisional application No. 60/044,037, filed on May 30, 1997, now abandoned, and provisional application No. 60/039,688, filed on Feb. 13, 1997, now abandoned.

(51) Int. Cl.[7] .......................... H05B 33/14; C09K 11/00

(52) U.S. Cl. ...................... 428/690; 428/917; 313/504; 313/506; 252/301.16; 546/10; 546/12; 546/13; 546/113; 546/264

(58) Field of Search ................................ 428/690, 917; 313/504, 506; 252/301.26, 301.31, 301.16; 546/8, 10, 12, 13, 255, 264, 276.4, 276.7, 113

(56) References Cited

U.S. PATENT DOCUMENTS

| | | | |
|---|---|---|---|
| 5,112,759 | * 5/1992 | Senoo et al. | 430/58 |
| 5,141,671 | 8/1992 | Bryan et al. | 252/301.16 |
| 5,150,006 | 9/1992 | Van Slyke et al. | 313/504 |
| 5,151,629 | 9/1992 | Van Slyke | 313/504 |
| 5,216,134 | 6/1993 | Mukkala et al. | . |
| 5,405,709 | 4/1995 | Littman et al. | 428/690 |
| 5,405,710 | 4/1995 | Dodabalapur et al. | 428/690 |
| 5,432,014 | 7/1995 | Sano et al. | 428/690 |
| 5,466,392 | 11/1995 | Hironaka et al. | 252/301.16 |
| 5,484,922 | 1/1996 | Moore et al. | . |
| 5,516,577 | 5/1996 | Matsuura et al. | 428/212 |

FOREIGN PATENT DOCUMENTS

| | | |
|---|---|---|
| 0 579 151 A | 1/1994 | (EP) . |
| 1668964 A | * 8/1991 | (SU) . |

OTHER PUBLICATIONS

Rolf Koppang, "Substitution of Hexafluorobenzene with Anilides", Journal of Organometallic Chemistry, 46 (1972), pp. 193–200, (no month).*
Wang et al., "A Novel Bonding Mode of a Deprotonated Syn–Anti 2,2'–Dipyridylamine Ligand to Dimethyl Aluminium . . . ", Polyhedron, vol. 15, No. 20, Jul. 1996, pp. 3543–3546.*
AN 1996:452862 ZCAPLUS, abstract for Engelhardt et al., "Monomeric, N–functionalized amido complexes of aluminum . . .", J. Chem. Soc., Dalton Trans., 1996, pp. 3053–3057, (no month).*
AN 1982:520158 ZCAPLUS, abstract for Lagutkin et al., "Antiviral activity of boron chelates synthesized from 2–aminopyridine", Khim.–Farm. Zh., 1982, pp. 695–699, (no month).*
Grem, G. et al., "Realization of a blue–light–emitting device using poly(p–phenylene)", Adv. Mater., 4:36–37 (1992), (no month).
Liu, W. et al., "Synthesis, crystal structures, and luminescent properties of aluminum complexes", Poster, Montreal and Southwestern Ontario Inorganic Chemistry Discussion Weekend Meeting, McGill University, Montreal, Quebec, Canada (Nov. 2, 1996).
Ohmori, Y. et al., "Blue electroluminescent diodes utilizing poly(alkylfluorene)", Jap. J. App. Phys., 30:L1941–L1943 (Nov. 1991).
Pei, Q., et al., "Efficient photoluminescence and electroluminescence from a soluble polyfluorene", J. Am. Chem. Soc. 118:7416–7417 (1996), (no month).
Pei, Q. et al., "Polymer light–emitting electrochemical cells: in situ formation of a light–emitting p–n junction", J. Am. Chem. Soc., 118:3922–3929 (1996) (no month).
Poort, S.H.M. et al., "Luminescence of $Eu^{2+}$ in barium and strontium aluminate and gallate", Chem. Mater., 7:1547–1551 (1995) (no month).
Rack, P.D. et al., "Materials used in electroluminescent displays", MRS Bulletin, pp. 49–58 (Mar., 1996).
Shirota, Y. et al., "Multilayered organic electroluminescent device using a novel starburst molecule, 4,4',4"–tris (3–methylphenylphenylamino)triphenylamine, as a hole transport material, Appl. Phys. Lett., 65:807–809 (Aug. 1994).
Tachelet, W. et al., "Blue electroluminescent devices with high quantum efficiency from alkoxy–substituted poly(para–phenylene vinylene)–trimers in a polystyrene matrix", Appl. Phys. Lett. 64:2364–2366 (May 1994).
Tsutsui, T., "Progress in electroluminescent devices using molecular thin films", MRS Bulletin, pp. 39–45 (Jun., 1997).
Wheeler, J.P., "Light–emitting polymers are ready for prime time", Photonics Spectra pp. 130–134 (Apr., 1997).
Yamamoto, T. et al., "Polymer light–emitting diodes with single– and double–layer structures using poly(2,3–diphenylquinoxaline–5,8–diyl)", Jpn. J. Appl. Phys. 33:L250–L253 (Feb. 1994).
Yang, Y. et al., "Polyaniline as a transparent electrode for polymer light–emitting diodes: lower operating voltage and higher efficiency", Appl. Phys. Lett. 64:1245–1247 (Mar. 1994).

* cited by examiner

Primary Examiner—Marie Yamnitzky
(74) Attorney, Agent, or Firm—Carol Miernicki Steeg

(57) ABSTRACT

Heterocyclic organoaluminum and organoboron coordination complexes that are photoluminescent and electroluminescent, emitting intense blue light. Methods of synthesizing such compounds, methods of producing photoluminescence and electroluminescence, methods of applying the compounds in thin films, and uses of the compounds of the invention in luminescent probes, electroluminescent displays and the like.

38 Claims, 28 Drawing Sheets

$Al_2(CH_3)_4(azain)_2$

R = Phenyl, Ph-azain

R = Methyl, Me-azain

Pentafluorophenyl-2-pyridylamine (PFPA)

Al$_3$(CH$_3$)$_3$(O)(Ph-azain)$_4$ $Al_3(CH_3)_3(O)(CH_3\text{-azain})_4$

Al(PFPA)$_3$

Structure of (7-azaindole)triphenylborane

An EL display device

LUMINESCENT COMPOUNDS AND METHODS OF MAKING AND USING SAME

CROSS-REFERENCE TO RELATED APPLICATIONS

This application is related to U.S. Ser. No. 60/039,688, filed Feb. 13, 1997, and U.S. Ser. No. 60/044,037, filed May 30, 1997, both now abandoned, the contents of which are hereby incorporated herein in their entirety.

FIELD OF THE INVENTION

The invention relates to compounds having luminescent properties, and to methods of synthesizing and using such compounds. The invention more particularly relates to compounds having photoluminescent and/or electroluminescent properties, and to synthesis and uses of same.

BACKGROUND OF THE INVENTION

A variety of luminescent compounds are known in the art. Green and red luminscent compounds are not uncommon, but blue luminescent metal ions and molecules are rare and generally expensive.

Two types of blue luminescent inorganic coordination compounds are known in which a heterocyclic chromophore includes a metal center coordinated by nitrogen and oxygen atoms of organic ligands. One type is based on 8-hydroxyquinoline and derivatives thereof, and the other is based on azomethine and derivatives thereof. Both the 8-hydroxyquinoline- and azomethine-based systems usually require several steps of synthesis and modification in order to achieve blue luminescence. The usefulness of these two systems in practical electroluminescence applications is limited, and blue luminescent materials with improved properties are desirable.

Production of devices based on electroluminescent display, and in particular on flat panel display, is a rapidly growing, billion dollar industry. Blue luminescent materials, as one of the key color components for electroluminescence display devices, are among the most sought-after materials by industry around the world.

SUMMARY OF THE INVENTION

It is an object of the present invention to provide blue luminescent compounds with improved properties. Another object of the invention is to provide improved luminescent products including such a compound. As used herein, the term "compound" includes coordination complexes, sometimes referred to simply as "complexes". The term "aliphatic" includes alkyl, alkenyl and and alkynyl, and straight and branched chain.

The invention provides compounds having the following formulas:

| | |
|---|---|
| $[AlR_2(azain)]_n$, | (i) |
| $[AlR_2(dpa)]_n$, | (ii) |
| $[Al_4R_6O_2(dpa)_2]$, | (iii) |
| $Al(PFPA)_3$, and | (iv) |
| derivatives of (i), (ii), (iii) and (iv), | (v) | where R is aliphatic, aryl or alkoxyl, azain is deprotonated 7-azaindole, dpa is deprotonated di-2-pyridyl amine, and PFPA is deprotonated pentafluorophenyl-2-pyridylamine.

The compounds are photoluminescent and, in at least some embodiments of the invention, they are electroluminescent; they produce intense blue light.

The invention also provides compounds having the following formulas:

| | |
|---|---|
| $Al_2R_2(azain)_4$, | (i) |
| $Al_2(R)(azain)_2(OR')_3$, | (ii) |
| $Al_3(R)(azain)_4(OR')_2(O)$, | (iii) |
| $Al_3R_3(azain)_4(O)$, and | (iv) |
| derivatives of (i), (ii), (iii) and (iv) | (v) | where R and R' are aliphatic, aryl or alkoxyl groups, azain is deprotonated 7-azaindole, and dpa is deprotonated di-2-pyridyl amine. The compounds are photoluminescent and, in at least some embodiments of the invention, they are electroluminescent; they produce intense blue light.

The invention further provides corresponding compounds wherein aluminum is replaced by boron. Such corresponding compounds include compounds having the following formulas:

| | |
|---|---|
| $B(dpa)X_2$, | (i) |
| $[BR_2(azain)]_n$ | (ii) |
| $B_2R_2(azain)_2(O)$, | (iii) |
| $BR_3(azainH)$, and | (iv) |
| derivatives of (i), (ii), (iii) and (iv), (v) | (v) | where azain is deprotonated 7-azaindole, dpa is deprotonated di-2-pyridyl amine, X is halide or alkoxyl, and R is aliphatic, aryl or alkoxyl.

Such corresponding compounds also include compounds having the following formulas:

| | |
|---|---|
| $[BR(dpa)_2]_n$ | (i) |
| $[BR_2(dpa)]_n$ and | (ii) |
| derivatives of (i) and (ii) | (iii) | where dpa is deprotonated di-2-pyridyl amine, and R and R' are aliphatic, aryl or alkoxy groups.

The boron compounds of the invention are photoluminescent and, in at least some embodiments of the invention, they are electroluminescent; they produce intense blue light.

The term "derivatives" includes compounds where derivatives of 7-azaindole (e.g., phenyl-7-azaindole, methyl-7-azaindole, disubstituted compounds, and the like) and derivatives of di-2-pyridyl amine are subsituents of the compounds, as discussed below. In certain embodiments of the invention, these may provide advantageous physical or chemical properties.

The invention provides a method of synthesizing a compound of the invention including the step:

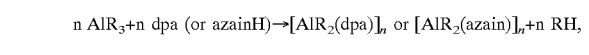

where (n=1 or 2).

The invention further provides a method of synthesizing a compound of the invention including the step:

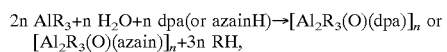

and $$AlR_3 + 3 PFPA\text{-}H \rightarrow Al(PFPA)_3 + 3 RH.$$

The invention also provides a method of synthesizing a compound of the invention including a step selected from the following group:

$$2\ AlR_3 + 4\ azainH \rightarrow Al_2R_2(azain)_4 + 4RH,$$

$$2\ AlR_3 + 2\ azainH + 3R'OH \rightarrow Al_2(R)(azain)_2(OR')_3 + 5RH,$$

$$3\ AlR_3 + 4\ azainH + H_2O + 2R'OH \rightarrow Al_3(R)(azain)_4(OR')_2(O) + 8RH,$$

and $$3AlR_3 + 4\ azainH + H_2O \rightarrow Al_3(R)_3(azain)_4(O) + 6RH,$$

where R and R' are aliphatic, aryl or alkoxy groups.

The invention further provides a method of synthesizing a compound of the invention including a step selected from the following group:

$$n\ BR_3 + n\ azainH \rightarrow [BR_2(azain)]_n + n\ RH(n=1,2),$$

$$2\ BR_3 + 2\ azainH + H_2O \rightarrow B_2R_2(azain)_2(O) + 4RH,$$

and $$BR_3 + azainH \rightarrow BR_3(azainH)$$

where R and R' are aliphatic, aryl or alkoxy groups.

The invention also provides a method of synthesizing a compound of the invention including a step selected from the following group:

$$n\ BR_3 + 2n\ dpa \rightarrow [BR(dpa)_2]_n + 2n\ RH$$

and $$n\ BR_3 + n\ dpa \rightarrow [BR_2(dpa)]_n + n\ RH,$$

where R and R' are aliphatic, aryl or alkoxy groups.

The invention provides a method of producing photoluminescence comprising the steps of: providing a photoluminescent compound of the invention having a formula as set out above (or a derivative thereof); and irradiating said photoluminescent compound with radiation of a wavelength suitable for exciting the compound to photoluminesce.

The invention provides a method of producing electroluminescence comprising the steps of: providing an electroluminescent compound of the invention having a formula as set out above (or a derivative thereof); and applying a voltage across said electroluminescent compound.

The invention further provides use of a compound of the invention as a component of a photoluminescent product or an electroluminescent product. For example, a luminscent compound could be used as a luminescent probe, or as a thin film in an electroluminescent display, such as a flat panel display device.

The invention still further provides an electroluminescent device for use with an applied voltage, comprising: a first electrode, an emitter (i.e., phosphor) which is an electroluminescent compound of the invention, and a second, transparent electrode, wherein a voltage is applied between the two electrodes to produce an electric field across the emitter. The emitter consequently electroluminesces. In some embodiments of the invention, the device includes one or more dielectric layers interposed between the emitter and one or more of the electrodes. For example, spacing of a preferred embodiment of the device is: first electrode, first dielectric layer, emitter, second dielectric layer, and second, transparent electrode.

In addition, the invention provides methods of applying compounds of the invention to a surface. These include chemical vapor deposition, spin coating and dip coating. The compounds may be applied alone or with a carrier. In some embodiments of the invention, they are applied in a composition including an organic polymer. Such compositions are also encompassed by the invention.

BRIEF DESCRIPTION OF THE DRAWINGS

For a better understanding of the present invention and to show more clearly how it may be carried into effect, reference will now be made by way of example to the accompanying drawings, which illustrate aspects and features according to preferred embodiments of the present invention, and in which.

DETAILED DESCRIPTION OF PREFERRED EMBODIMENTS

Two alternative ways in which a blue luminescent material could be achieved are: (i) providing a molecule which emits blue color (emitter), and (ii) doping an emitter to a suitable matrix such that the combination yields blue luminescence. The emitter can be either an inorganic metal ion such as lanthanide which emits blue light via d→f or f→f electronic transition, or an organic molecule which has conjugated π bonds and emits blue light via π→π or π→n electronic transitions.

The known inorganic blue emitters, lanthanide ions, have low emission efficiency and require the use of a host (generally an inorganic salt), which makes it difficult to process them into thin films. Only a few organic blue emitters are known to date. Those known organic blue emitters are typically extended π oligomers or polymers. They are not only difficult to synthesize, thus, very expensive for an industrial scale application, but also tend to have poor luminescence efficiency and poor stability. In addition, the applications of luminescent polymers are limited, as their poor volatility prevents them being applied as films using chemical vapor deposition (CVD), a process known to produce superior films for electroluminescence displays.

Figure 23:
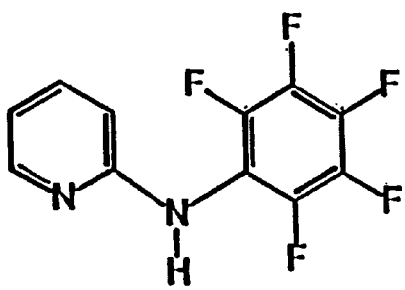
FIG. 23 shows the structure of pentafluorophenyl-2-pyridylamine (PFPA-H)

We have discovered new organoaluminum and organoboron compounds that exhibit intense blue luminescence. Organoaluminum compounds of the invention include: [AlR$_2$(azain)]$_n$, [AlR$_2$(dpa)]$_n$, [Al$_4$R$_6$O$_2$(dpa)$_2$], and Al(PFPA)$_3$ where R=aliphatic, aryl, alkoxyl; azain= deprotonated 7-azaindole (shown below); dpa=deprotonated di-2-pyridyl amine (shown below); and PFPA=deprotonated pentafluorophenyl-2-pyridylamine (see FIG. 23); as well as, Al$_2$R$_2$(azain)$_4$, Al$_2$(R)(azain)$_2$(OR')$_3$, Al$_3$(R)(azain)$_4$(OR')$_2$(O), and Al$_3$R$_3$(azain)$_4$(O), where R and R'=aliphatic, aryl, alkoxyl; azain=deprotonated 7-azaindole; dpa=deprotonated di-2-pyridyl amine. Organoboron compounds of the invention include: B(dpa)X$_2$, [BR$_2$(azain)]$_n$, B$_2$R$_2$(azain)$_2$(O), and BR$_3$(azainH), where azain=deprotonated 7-azaindole; dpa=deprotonated di-2-pyridyl amine; X=halide, alkoxyl; and R is aliphatic, aryl, alkoxyl; as well as, [BR(dpa)$_2$]$_n$ and [BR$_2$(dpa)]$_n$ where dpa=deprotonated di-2-pyridyl amine; and R and R'=aliphatic, aryl, alkoxy. Derivatives of these compounds are also encompassed by the invention. For photoluminescence, the compounds absorb energy from ultraviolet radiation and emit visible light in the blue region, i.e., near the ultraviolet end of the visible spectrum. For electroluminescence, the absorbed energy is from an applied electric field.

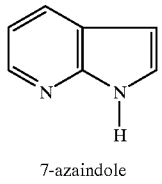
7-azaindole

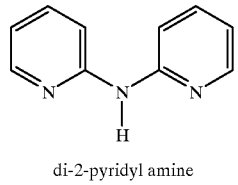
di-2-pyridyl amine

A typical reaction scheme is as follows:

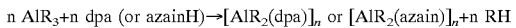
n AlR$_3$+n dpa (or azainH)→[AlR$_2$(dpa)]$_n$ or [AlR$_2$(azain)]$_n$+n RH Here, n is 1 or 2. The aliphatic, aryl or alkoxyl group R abstracts the acidic proton from di-2-pyridyl amine (or 7-azaindole) to form alkane (RH) or alcohol (ROH), respectively. In most embodiments of the invention, the desired product is conveniently produced in a single step.

Starting materials 7-azaindole and di-2-pyridyl amine are inexpensive and readily available from commercial sources. AlR$_3$ can be either purchased directly from commercial sources or synthesized by a one step metathesis reaction using commercially available trialkylaluminum (e.g., Al(CH$_3$)$_3$) as the starting material, as follows:

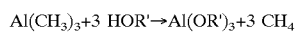
Al(CH$_3$)$_3$+3 HOR'→Al(OR')$_3$+3 CH$_4$

Thus, this starting material is also inexpensive and readily available.

Starting material pentafluorophenyl-2-pyridylamine (PFPA-H) is also readily produced by the method of R. Koppang, *J. Organometallic Chemistry*, 46, 193 (1972) (See Example 16).

Derivatives of starting materials 7-azaindole and di-2-pyridyl amine may also be employed to produce luminescent compounds of the invention. Examples 12 and 13 below illustrate preparation of phenyl-7-azaindole and methyl-7-azaindole, respectively. As would be apparent to a person of ordinary skill in the art, other functionalities than methyl and phenyl may be included in derivatives according to the invention. For example, 7-azaindole and di-2-pyridyl amine may be substituted on one or more carbons with an aliphatic (alkyl, alkenyl or alkynyl, straight or branched chain), aromatic, alkoxy, hydroxyl, halogen, amino, nitro, or nitrile group, —CF$_3$, or the like. Alternatively, starting materials 7-azaindole and di-2-pyridyl amine may be modified to include, but are not limited to, functionalities such as ether, epoxide, ester, amide or the like. Such functionalities may in some cases confer desirable physical or chemical properties, such as increased stability or luminescence.

The following is another typical reaction scheme which may be employed to yield a luminescent compound of the invention:

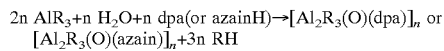
2n AlR$_3$+n H$_2$O+n dpa(or azainH)→[Al$_2$R$_3$(O)(dpa)]$_n$ or [Al$_2$R$_3$(O)(azain)]$_n$+3n RH Other typical reaction schemes according to the invention include a synthesis, as follows:

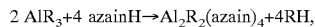
2 AlR$_3$+4 azainH→Al$_2$R$_2$(azain)$_4$+4RH,

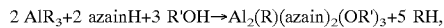
2 AlR$_3$+2 azainH+3 R'OH→Al$_2$(R)(azain)$_2$(OR')$_3$+5 RH,

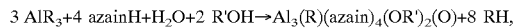
3 AlR$_3$+4 azainH+H$_2$O+2 R'OH→Al$_3$(R)(azain)$_4$(OR')$_2$(O)+8 RH,

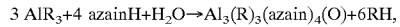
3 AlR$_3$+4 azainH+H$_2$O→Al$_3$(R)$_3$(azain)$_4$(O)+6RH, or

AlR$_3$+3PFPA-H Al(PFPA)$_3$+3RH, where R and R' are aliphatic, such as, for example, ethyl or iso-propyl, aryl or alkoxy groups, and PFPA is deprotonated pentafluorophenyl-2-pyridylamine.

Other typical reaction schemes according to the invention include a synthesis, as follows:

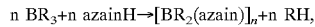
n BR$_3$+n azainH→[BR$_2$(azain)]$_n$+n RH, (n=1, 2),

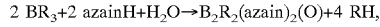
2 BR$_3$+2 azainH+H$_2$O→B$_2$R$_2$(azain)$_2$(O)+4 RH, or

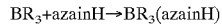
BR$_3$+azainH→BR$_3$(azainH)

where R and R' are aliphatic, such as, for example, ethyl or iso-propyl, aryl or alkoxy groups. A particularly preferred compound according to this aspect of the invention, which has been shown to exhibit blue photoluminescence and blue electroluminescence, is $B_2(C_2H_5)_2(azain)_2(O)$, for which a preferred synthetic protocol is described in Example 11. Other particularly preferred compounds according to this aspect of the invention are $BR_3(azain)$, where R is phenyl or phenoxy (see Examples 18 and 19). These compounds also demonstrate strong photoluminescence and are easy to synthesize.

Still other typical reaction schemes according to the invention include a synthesis, as follows:

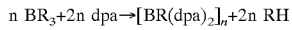

or

where R and R' are aliphatic, aryl or alkoxy groups.

Specific examples of syntheses according to preferred embodiments of the invention are given below in Examples 1–11.

In undertaking to achieve blue luminescent aluminum complexes with azaindole or dipyridyl amine, the inventors took into account the following physico-chemical reasoning: First, the desired compound should be colorless. As the aluminum(III) (Al(III)) ion does not have any d electrons and its compounds are usually colorless, the inventors reasoned that it would be a good candidate as a binding center for the organic ligands. Second, 7-azaindole and di-2-pyridyl amine can form extended $\pi$ structures upon coordinating to a metal center, and thus could potentially function as emitters through $\pi \rightarrow \pi$ or $n \rightarrow \pi$ transitions.

Figure 1:
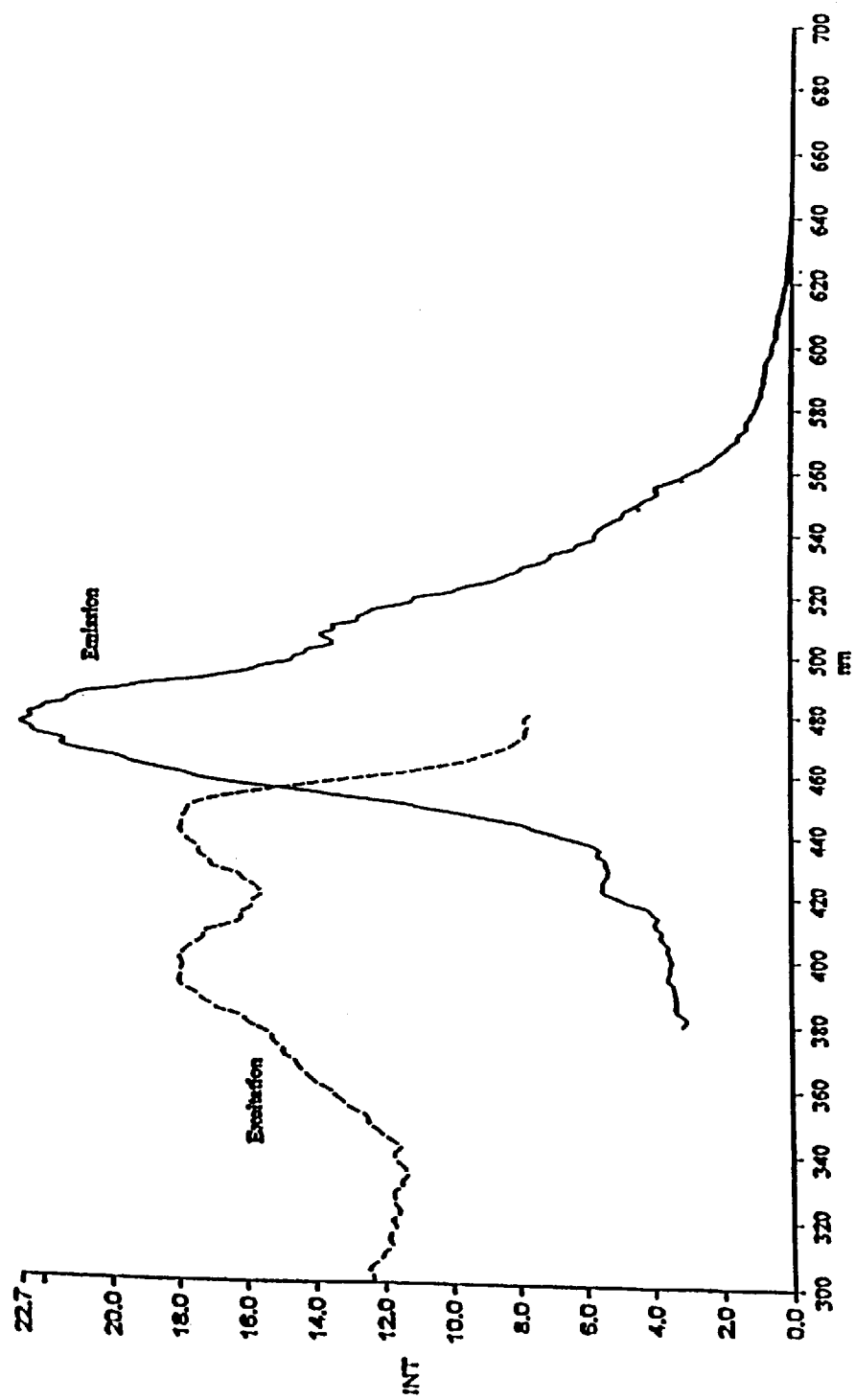
FIG. 1 shows the excitation and emission spectra of $Al(CH_3)_2(dpa)$.
Figure 2:
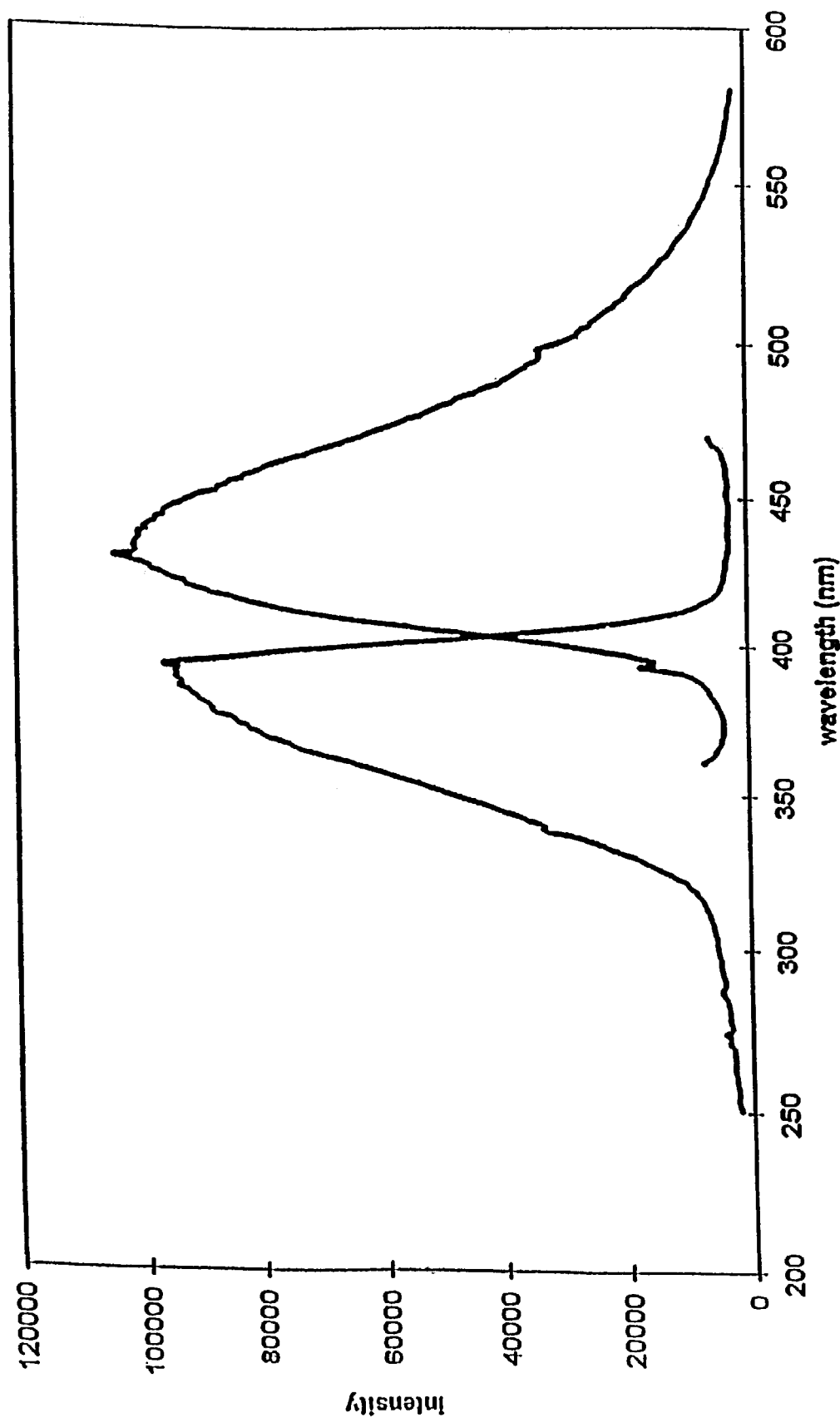
FIG. 2 shows the excitation and emission spectra of $Al_2(CH_3)_4(azain)_2$.

One advantage of combining an inorganic metal ion (Al(III)) with organic ligands (dpa, azaindole) is that the luminescence efficiency of the organic chromophore is enhanced. The coordination of a metal center to an organic chromophore can increase the chromophore's structural rigidity, thereby reducing the probability of energy loss via a thermal non-radiation process and increasing the efficiency of emission. For example, we have discovered that di-2-pyridyl amine and 7-azaindole have only very weak luminescence at ambient temperature (23° C.), but upon coordinating to the aluminum center, the emission intensity increases dramatically. Both $Al(CH_3)_2(dpa)$ and $[Al(CH_3)_2(azain)]_2$ emit intense blue light as shown by their excitation and emission spectra, depicted in FIGS. 1 and 2. The formation of aluminum compounds with the organic ligands clearly played a key role in inducing the intense blue luminescence.

The inventors have shown that the analogous alkoxyl compounds $Al(OPr^i)_2(dpa)$ and $[Al(OPr^i)_2(azain)]_2$, where $Pr^i$=iso-propyl, demonstrate similar excitation and intense blue emission spectra. Other aliphatic substitutents are expected to have similar properties. The inventors have further demonstrated that the excitation and emission spectra of $Al(OR)_2(dpa)$ where R is an aryl group such as phenyl are similar to FIG. 1, and that the excitation and emission spectra of $Al_2(OR)_4(azain)_2$ where R is an aryl group such as phenyl are similar to FIG. 2. The inventors have still further demonstrated electroluminescence of $[Al(OPr^i)_2(azain)]_2$, as is described in detail in Example 6 below.

Figure 3:
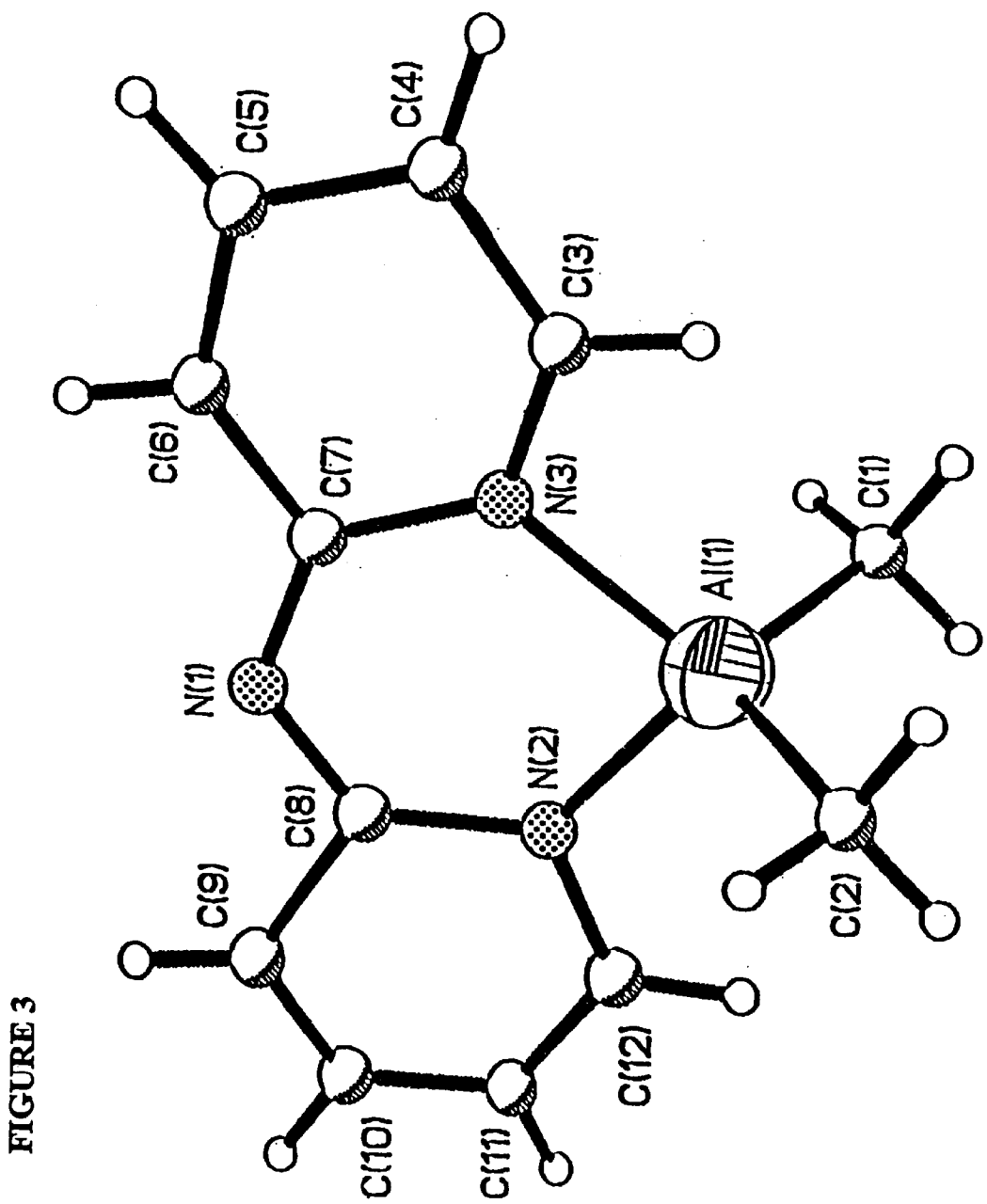
FIG. 3 shows the crystal structure of $Al(CH_3)_2(dpa)$.
Figure 4:
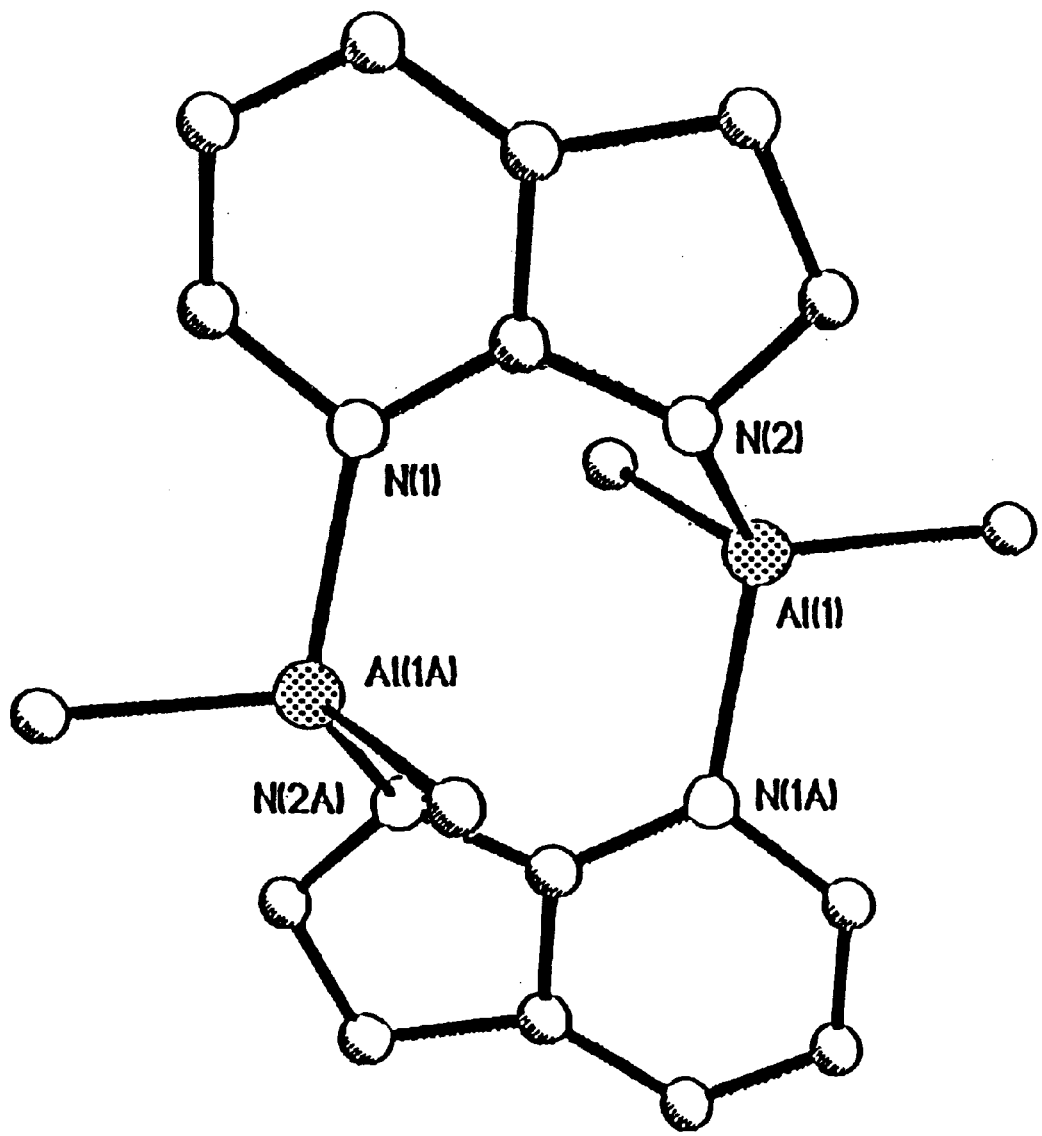
FIG. 4 shows the crystal structure of $Al_2(CH_3)_4(azain)_2$.
Figure 5:
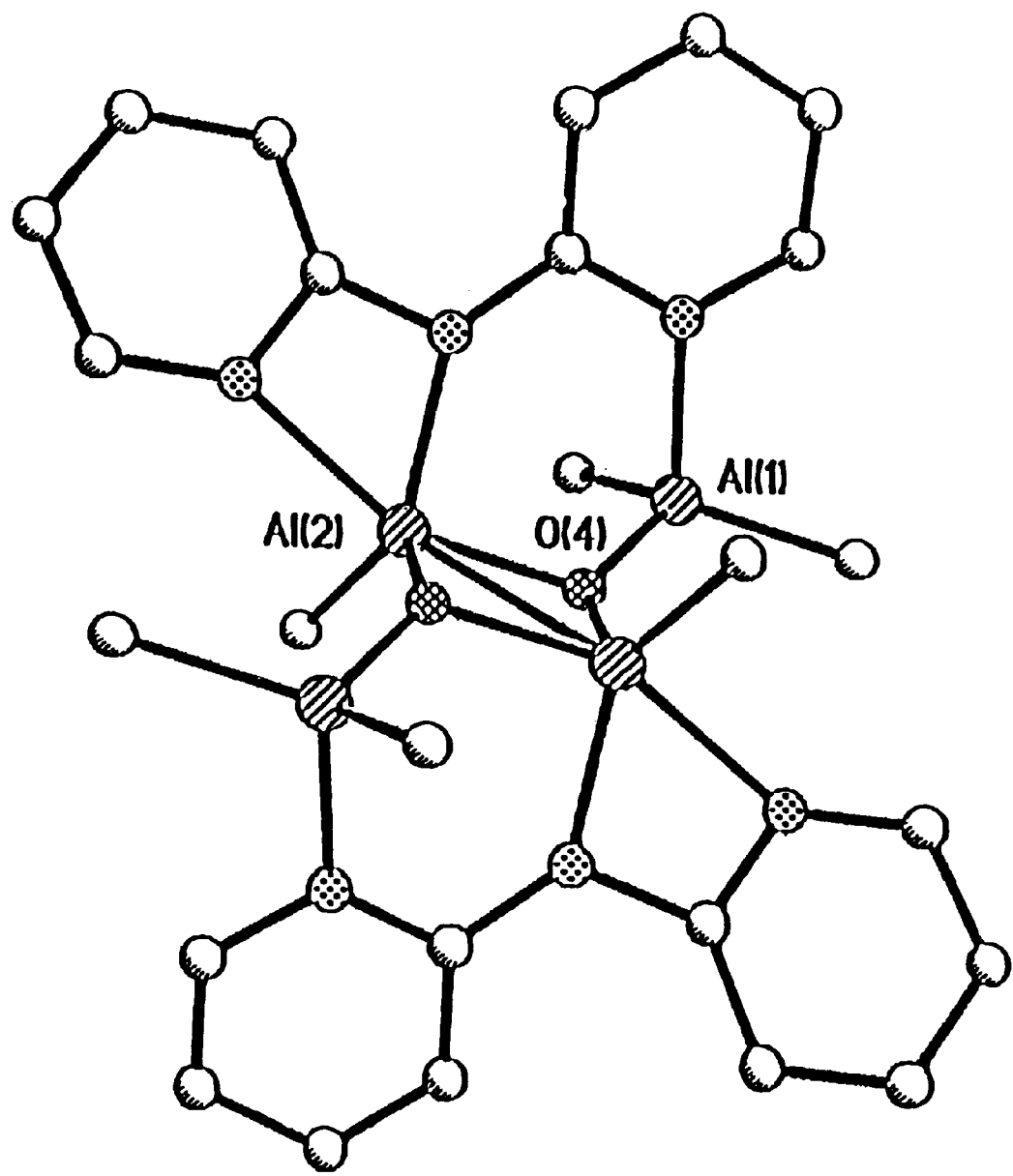
FIG. 5 shows the crystal structure of $Al_4(CH_3)_6(dpa)_2O_2$.

The molecular structures of $Al(CH_3)_2(dpa)$ and $[Al(CH_3)_2(azain)]_2$ have been determined by single-crystal X-ray diffraction analyses. Such analyses show that the dpa and the 7-azaindole ligands bind to the aluminum center either as a chelating ligand (the ligand binds to one aluminum center only) or as a bridging ligand (the ligand binds to two aluminum centers) (FIGS. 3–5). Apparently, the bond formation between the aluminum ion and the 7-azaindole or the dpa ligand is responsible for the high emission intensity of the blue luminescence produced by the complex.

Additional advantages provided by the compounds of the invention are improved stability and manageability for processing. In practical applications, it is often highly desirable for luminescent compounds to be processed to form high quality films. A superior way to achieve high quality films is by CVD, which requires the material to be thermally stable and sublimable under vacuum. Aluminum complexes as described herein demonstrate these desired properties. For example, the dimeric $[Al(CH_3)_2(azain)]_2$ compound is thermally stable up to 300° C. and can be sublimed at 0.07 mm Hg and 200° C.

The $[Al(CH_3)_2(azain)]_2$ compound can degrade slowly upon exposure to air, due to the reaction of the methyl group with moisture, but we have found ways to overcome this problem. For instance, since the luminescence does not depend on the methyl groups, they can be replaced with more inert alkoxyl groups without destroying the luminescence. This can be achieved either by reacting 7-azaindole with $Al(OR)_3$ directly or by reacting $[Al(CH_3)_2(azain)]_2$ with four equivalent HOR to form the $[Al(OR)_2(azain)]_2$ compound. The inventors have shown that the analogous alkoxyl compounds $Al(OPr^i)_2(dpa)$ and $[Al(OPr^i)_2(azain)]_2$ can, like the alkyl compounds, be sublimed readily.

The volatility of a compound of the invention can be modified by modifying the R group: in general, the bulkier the R group, the more sublimable the compound, due to the decreased attractive intermolecular interactions in the crystal lattice. It is possible to replace some of the methyl groups with hydroxyl ($OH^-$) or oxygen ($O^{2-}$) ligand by introducing moisture into the reaction medium. For example, $Al(CH_3)_3$ reacts with dpa in the presence of 0.5 equivalent $H_2O$ to form the tetranuclear complex $Al_4(CH_3)_6(O)_2(dpa)_2$ (FIG. 5), which is much more stable than $Al(CH_3)_2(dpa)$ toward air and emits intense blue light as well.

Yet a further advantage of luminescent compounds of the invention is that they are highly soluble in common organic solvents such as toluene, diethyl ether, tetrahydrofuran (THF) and dichloromethane. This permits the compounds to be blended easily and conveniently with organic polymers. The role of the organic polymer in such a mixture is at least two-fold: First, a polymer can provide protection for the luminscent compound from air degradation. Second, a polymer host matrix permits the use of a spin-coating or dip-coating process as an alternative way to make luminescent films. Although spin-coating and dip-coating processes may not produce as high quality films as those produced by CVD, they are often much faster and more economical than CVD.

Figure 6:
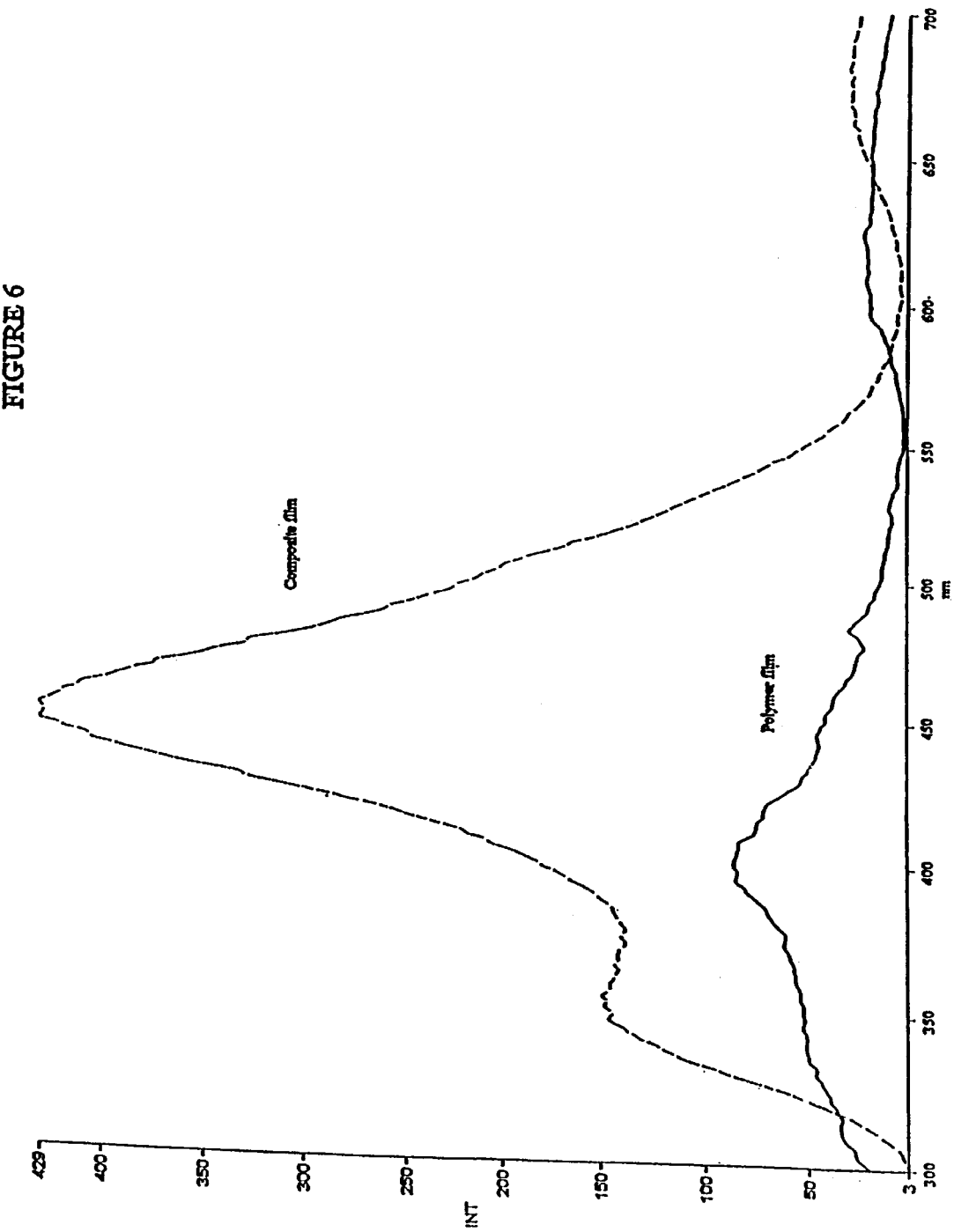
FIG. 6 shows the emission spectrum of $Al_2(CH_3)_4(azain)_2$ in a poly(methyl methacrylate) matrix (dashed line) and the emission spectrum of the pure poly(methyl methacrylate)
Figure 7:
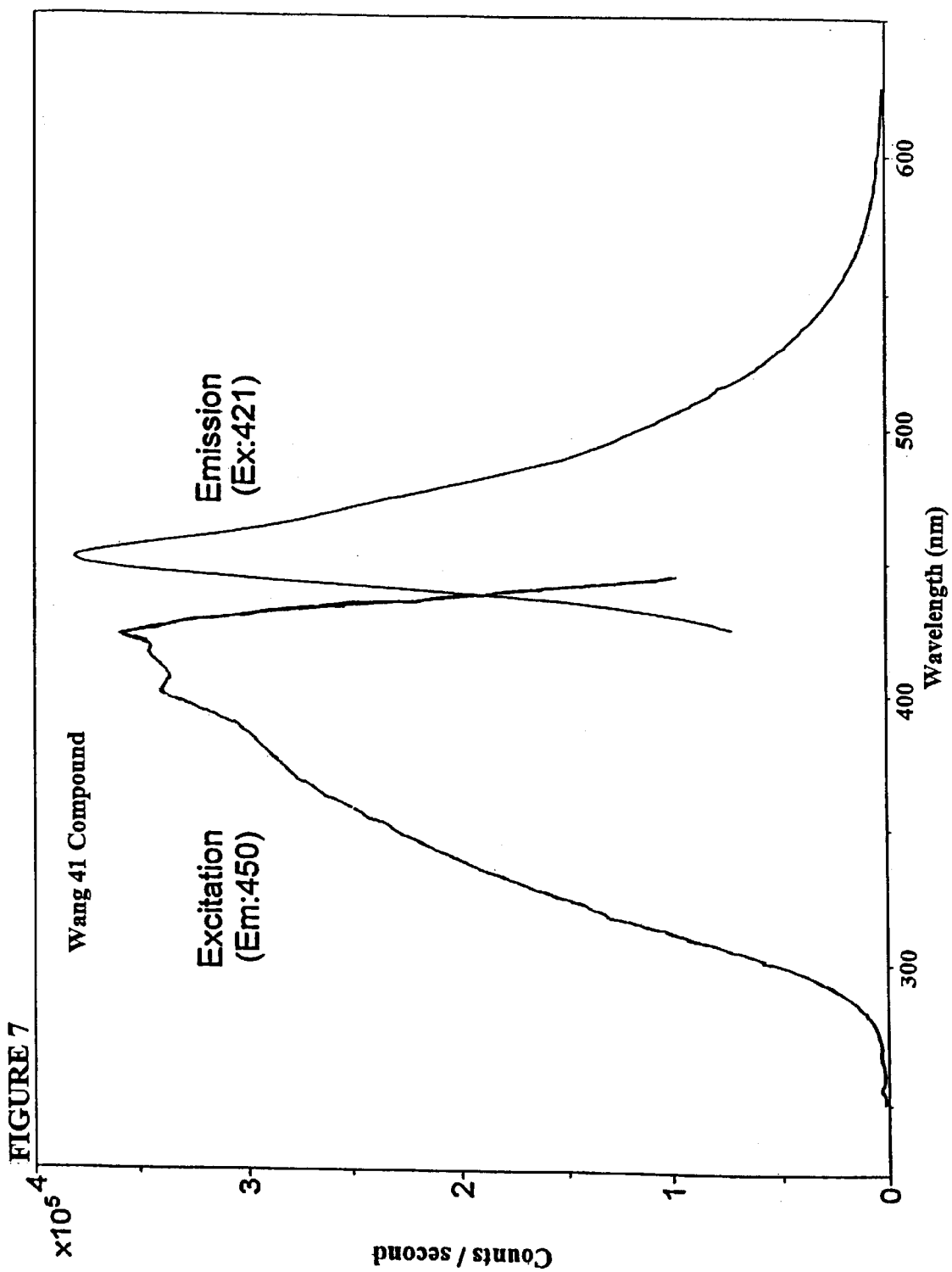
FIG. 7 shows the excitation and emission spectra of $Al_4(CH_3)_6(dpa)_2O_2$.

As an example of this application, the $[Al(CH_3)_2(azain)]_2$ compound forms a clear transparent solution with the non-luminescent polymer poly[1-(methoxycarbonyl)-1-methylethylene (poly(methyl methacrylate) in toluene. This can be converted to a transparent film by evaporating the toluene solvent via either a dip-coating or spin-coating process. Films obtained in this way are stable in air for days without losing the intense blue luminescence (FIG. 6). Certain polymers are expected to further enhance the luminescence of the emitter in the film.

In some embodiments of the invention, we have replaced the aluminum ion with boron, to further enhance the stability of the coordination complex. B—C, B—N, and B—O bonds in general are more covalent in nature than the corresponding aluminum bonds, and are therefore less susceptible to degradation by air and moisture. In addition, boron compounds have less tendency to form aggregates or oligomers, and are therefore generally more volatile than corresponding aluminum compounds. For example, B(dpa)$X_2$, where X is halide or alkoxyl, has been found to produce blue luminescence, is stable in air and is sublimable. Specific examples of blue luminescent boron coordination complexes according to the invention are described in Examples 10 and 11 below.

The invention provides a method of producing electroluminescence comprising the steps of: providing an electroluminescent compound of the invention having a formula as set out above (or a derivative thereof); and applying a voltage across said electroluminescent compound so that the compound electroluminesces.

According to the invention, electroluminescent devices for use with an applied voltage are provided. In general, such a device has a first electrode, an emitter which is an electroluminescent compound of the invention, and a second, transparent electrode, wherein a voltage is applied between the two electrodes to produce an electric field across the emitter of sufficient strength to cause the emitter to electroluminesce. Preferably, the first electrode is of a metal, such as, for example, aluminum, which reflects light emitted by the compound; whereas the second, transparent electrode permits passage of emitted light therethrough. The transparent electrode is preferably of indium tin oxide (ITO) glass or an equivalent known in the art. Here, the first electrode is the cathode and the second electrode is the anode.

Figure 29:
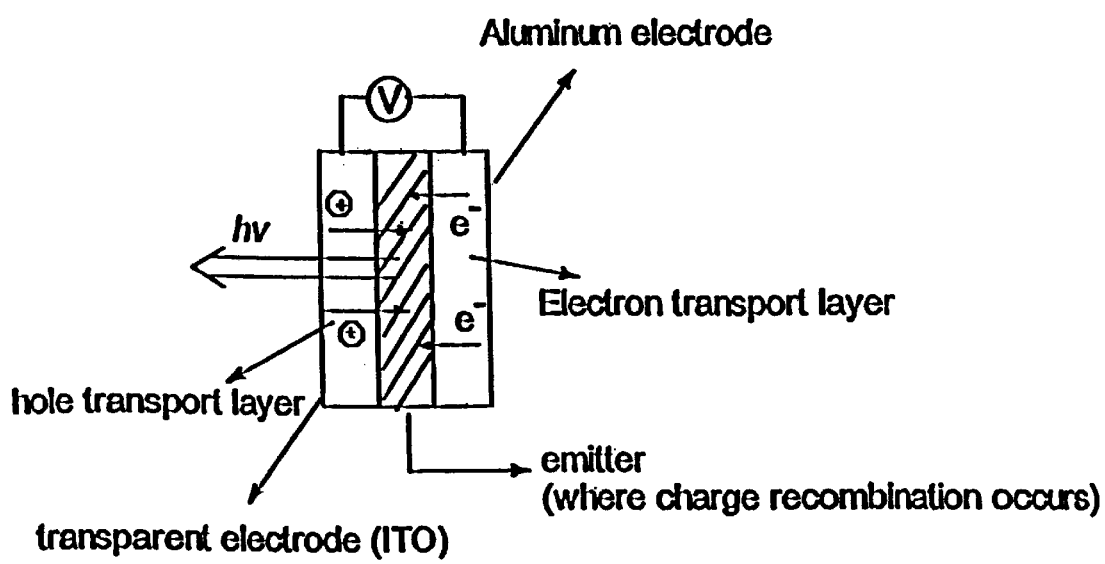
FIG. 29 shows a preferred embodiment of a electroluminescent (EL) display device according to the invention.

Referring to FIG. 29, a preferred embodiment of an electroluminescent device of the invention is shown. The emitter is interposed between an electron transport layer (e.g., Alq, BND, TAZ) adjacent the metal first electrode and a hole transport layer (e.g., TPD, α-NPD, mTADATA) adjacent the second, transparent electrode. The choice of the materials employed as hole and electron transport layers will depend upon the specific properties of the particular emitter employed. The hole or electron transport layer may also function as a supporting layer. The device is connected to a voltage source such that an electric field of sufficient strength is applied across the emitter. Blue light consequently emitted from the compound of the invention passes through the transparent electrode.

In some embodiments of the invention, the device includes one or more dielectric layers interposed between the emitter and one or both of the electrodes. Such dielectric layer(s) are employed in prior art systems with inorganic salt emitters to reduce the voltage drop across the emitter. In a first example of such a device, layers are arranged in a sandwich in the following order: first electrode, dielectric layer, emitter, and second, transparent electrode. In a preferred embodiment of this type, a substrate of glass, quartz or the like is employed. A reflective metal layer (corresponding to the first electrode) is deposited on one side of the substrate, and an insulating dielectric layer is deposited on the other side. The emitter layer which is a compound of the invention is deposited on the dielectric layer, preferably by CVD, though other methods may be equally effective. A transparent conducting ITO is then deposited on the emitter layer. An effective voltage is applied to produce electroluminescence of the emitter.

In a second example of an EL device of the invention a second dielectric layer is employed, the sandwich layers are arranged in the following order: first electrode, first dielectric layer, emitter, second dielectric layer and second, transparent electrode.

Electroluminescent devices of the invention may include one or more of the blue-emitting compounds described herein. Such devices may be flat panel display devices. In some embodiments of the invention, an electroluminscent device such as a flat panel display device may include not only a blue-emitting phosphor as described herein, but may be a multiple-color display device including one or more other phosphors. The other phosphors may emit in other light ranges, i.e., red, green, and/or be "stacked" relative to each other. Convenient materials, structures and uses of electroluminescent display devices are described in P. D. Rack et al., *MRS Bulletin,* pp. 49–58 (March 1996).

All scientific and patent publications cited herein are hereby incorporated in their entirety by reference.

EXAMPLES

Example 1

Synthesis of [Al(CH$_3$)$_2$(azain)]$_2$ 0.50 mmol of 7-azaindole was dissolved in 10 mL of toluene under nitrogen. 0.50 mmol Al(CH$_3$)$_3$ (0.25 mL of 2 M Al(CH$_3$)$_3$ solution in hexane) was added to the solution at 23° C. The mixture was stirred for 1.5 h. The solution was concentrated to about 5 mL. The product [Al(CH$_3$)$_2$(azain)]$_2$ was isolated as colorless crystals, at 60% yield.

Example 2

Synthesis of Al(CH$_3$)$_2$(dpa)

0.50 mmol of di-2-pyridyl amine was dissolved in 10 mL of toluene under nitrogen. 0.5 mmol Al(CH$_3$)$_3$ (0.25 mL of 2 M Al(CH$_3$)$_3$ solution in hexane) was added to the solution at 23° C. The mixture was stirred for 3.0 h. The solution was concentrated to about 5 mL. The product Al(CH$_3$)$_2$(dpa) was isolated as colorless crystals, at >60% yield.

Example 3

Synthesis of [Al$_2$(CH$_3$)$_3$O (dpa)]$_2$ 1 mmol of di-2-pyridyl amine was dissolved in 10 mL of toluene under nitrogen. 0.5 mmol Al(CH$_3$)$_3$ (0.25 mL of 2 M Al(CH$_3$)$_3$ solution in hexane) was added to the solution at 23° C. 0.25 mmol of H$_2$O in toluene was added. The mixture was stirred for 3.0 h. The solution was concentrated to about 5 mL. The product [Al$_2$(CH$_3$)$_3$O (dpa)]$_2$ was isolated as colorless crystals, at >50% yield.

Example 4

Synthesis of [Al(OPr$^i$)$_2$(azain)]$_2$ 0.5 mmol of 7-azaindole was dissolved in 15 mL of toluene under nitrogen. 0.50 mmol Al(OPr$^i$)$_3$ was added to the solution at 23° C. The mixture was stirred 0.5 h at 23° C. and 0.5 h at 80° C. The solution was evaporated to dryness in vacuum. The colorless powder product [Al(OPr$^i$)$_2$(azain)]$_2$ was purified by sublimation at 80° C. and 0.04 mm Hg.

Example 5

Synthesis of Al(OPr$^i$)$_2$(dpa)

Compound Al(OPr$^i$)$_2$(dpa) was prepared by the same procedure as [Al(OPr$^i$)$_2$(azain)]$_2$ except that 7-azaindole was replaced by di-2-pyridyl amine.

Example 6

Electroluminescence of [Al(OPr$^i$)$_2$(azain)]$_2$

Electroluminescence of [Al(OPr$^i$)$_2$(azain)]$_2$ was demonstrated using the shadow mask technique described in X. Yu and M. Sayer, "Thin film electroluminescent displays", *J. Can. Ceram. Soc.* 55: 1 (1986), the contents of which are hereby incorporated by reference. According to one embodiment of this technique, two electrodes are provided that are, respectively, a first set of parallel lines applied using a shadow mask, and a second set of parallel lines perpendicular to the first set that are also applied using a shadow mask. A layer of test sample is interposed between the two electrodes, and an electric field is thereby applied to the sample.

A sample of 200 mg of $[Al(OPr^i)_2(azain)]_2$ was dissolved in 3 mL of $CH_2Cl_2$ at 23° C. The resulting solution was spin-coated onto indium tin oxide (ITO) coated glass having a first electrode in the form of an etched shadow mask pattern of parallel lines spaced 1 mm apart. The sample film so-produced was approximately 2 in ×1.5 in with a thickness of 2–4 μm. A second, aluminum electrode layer was patterned onto the surface of the $[Al(OPr^i)_2(azain)]_2$ film by metal evaporation through a shadow mask of parallel lines spaced 1 mm apart and perpendicular to the first set. (Thus, individual elements were 1 mm×mm×2–4 μm in size.) Silver paste was used to contact the ITO layer. Blue luminescence was observed at an applied voltage of approximately 50 V AC at 60 Hz and an injection current of 200–500 mA. In preferred embodiments of the invention, electroluminescence is improved by using higher quality films and/or a multiple layer device.

Example 7

Figure 8:
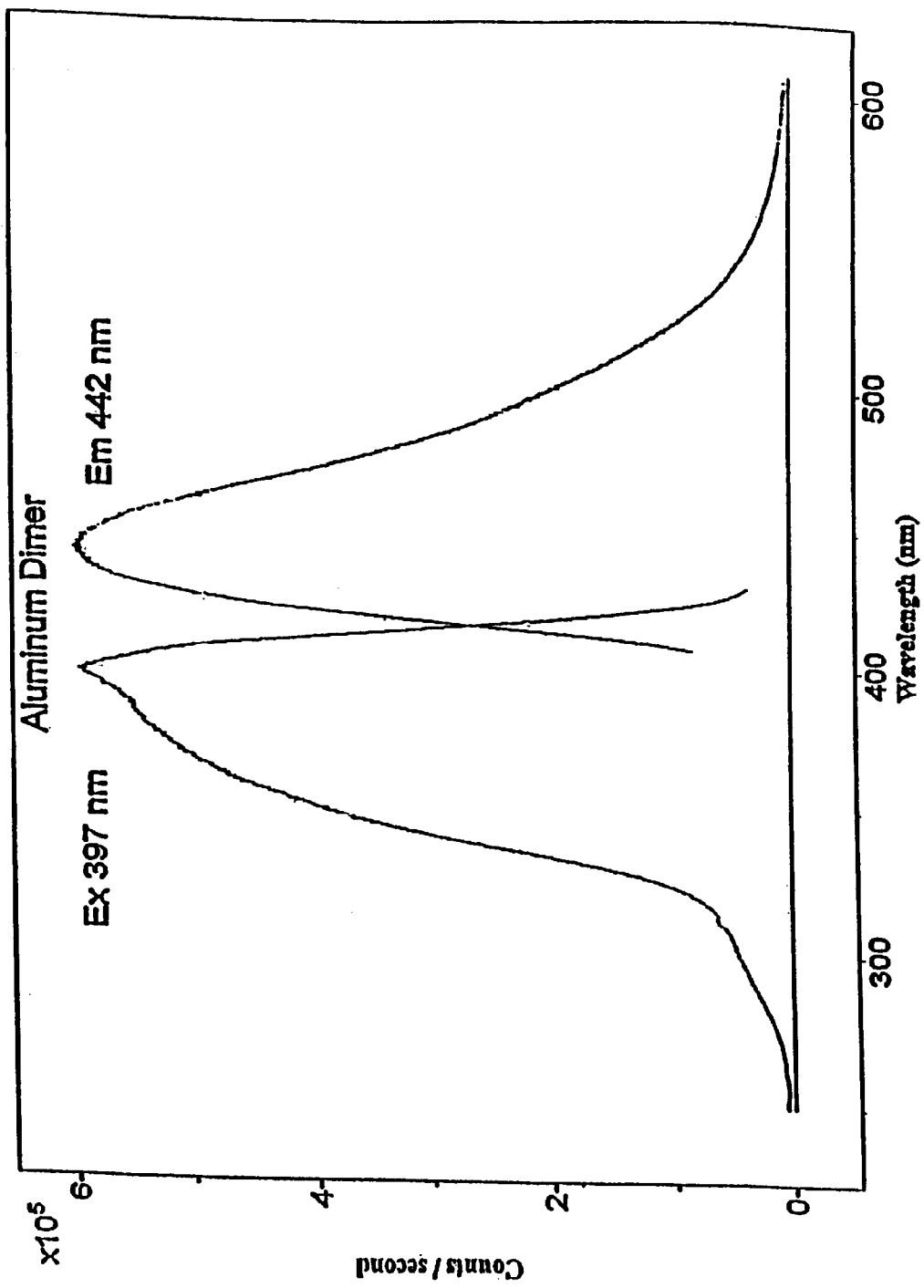
FIG. 8 shows the excitation and emission spectra of $Al(CH_3)_2(azain)_4$.
Figure 9:
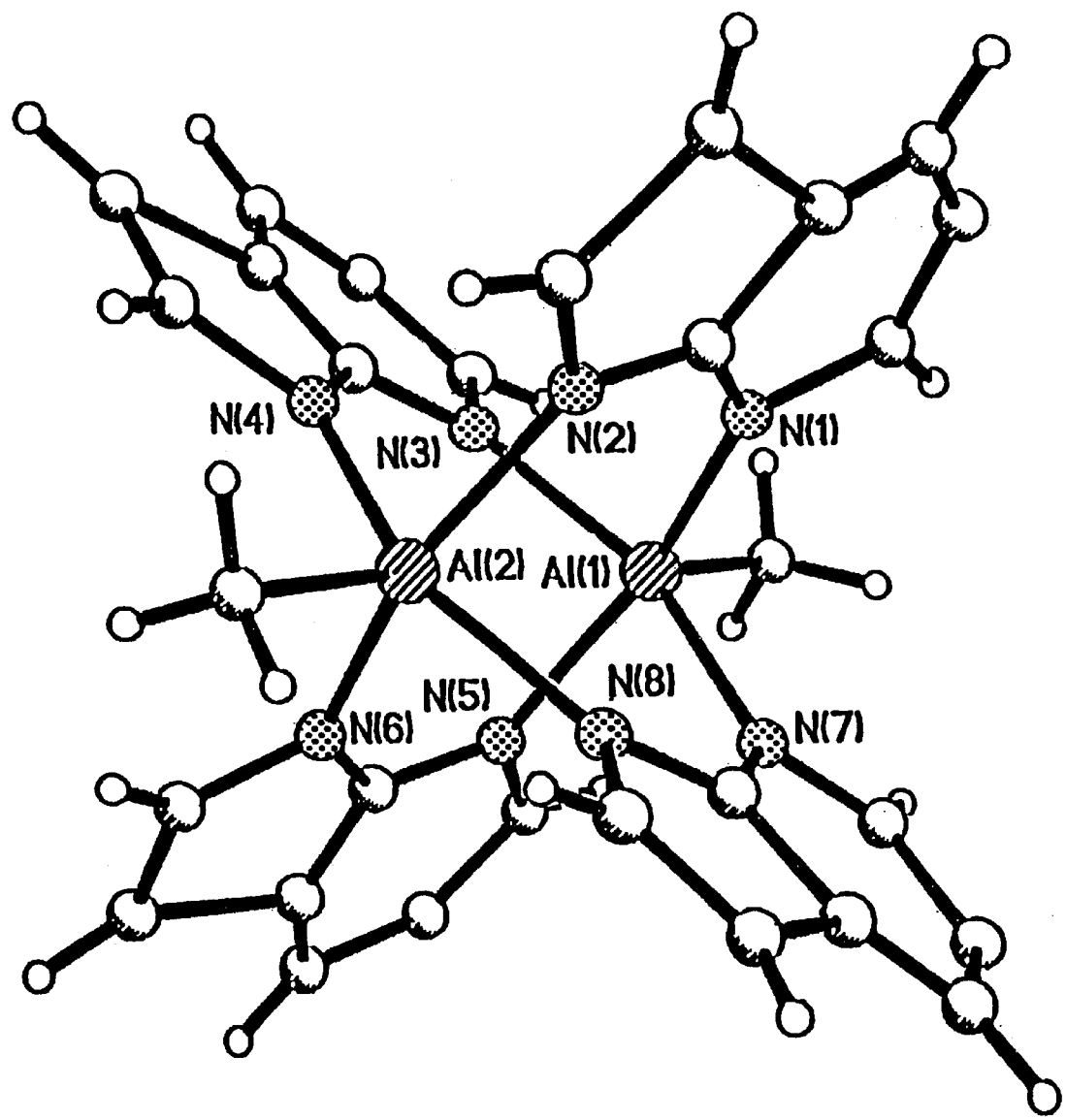
FIG. 9 shows the crystal structure of $Al(CH_3)_2(azain)_4$.

Synthesis of $Al_2(CH_3)_2(azain)_4$ 200 mg (1.70 mmol) of 7-azaindole in 8 mL of toluene was reacted with 423 mL (0.846 mmol) of $Al(CH_3)_3$ (2.0 M in hexane ) at 23° C. under nitrogen. The reaction mixture was stirred for 3 h. The volume of the solution was reduced to approximate 2 mL by vacuum. 2 mL of hexane was added to crystallize the product. After a few days standing at 23° C., colorless crystals of compound $Al_2(CH_3)_2(azain)_4$ were obtained in 62% yield. When excited by UV light (λ=397 nm), this compound emits blue color at ($\lambda_{max}$=442 nm (FIG. 8). The structure of compound $Al_2(CH_3)_2(azain)_4$ was determined by single-crystal X-ray diffraction analysis. There are four bridging 7-azaindole ligands in $Al_2(CH_3)_2(azain)_4$, as shown in FIG. 9.

Example 8

Synthesis of $Al_2(OCH(CF_3)_2)_3(azain)_2(CH_3)$

Figure 10:
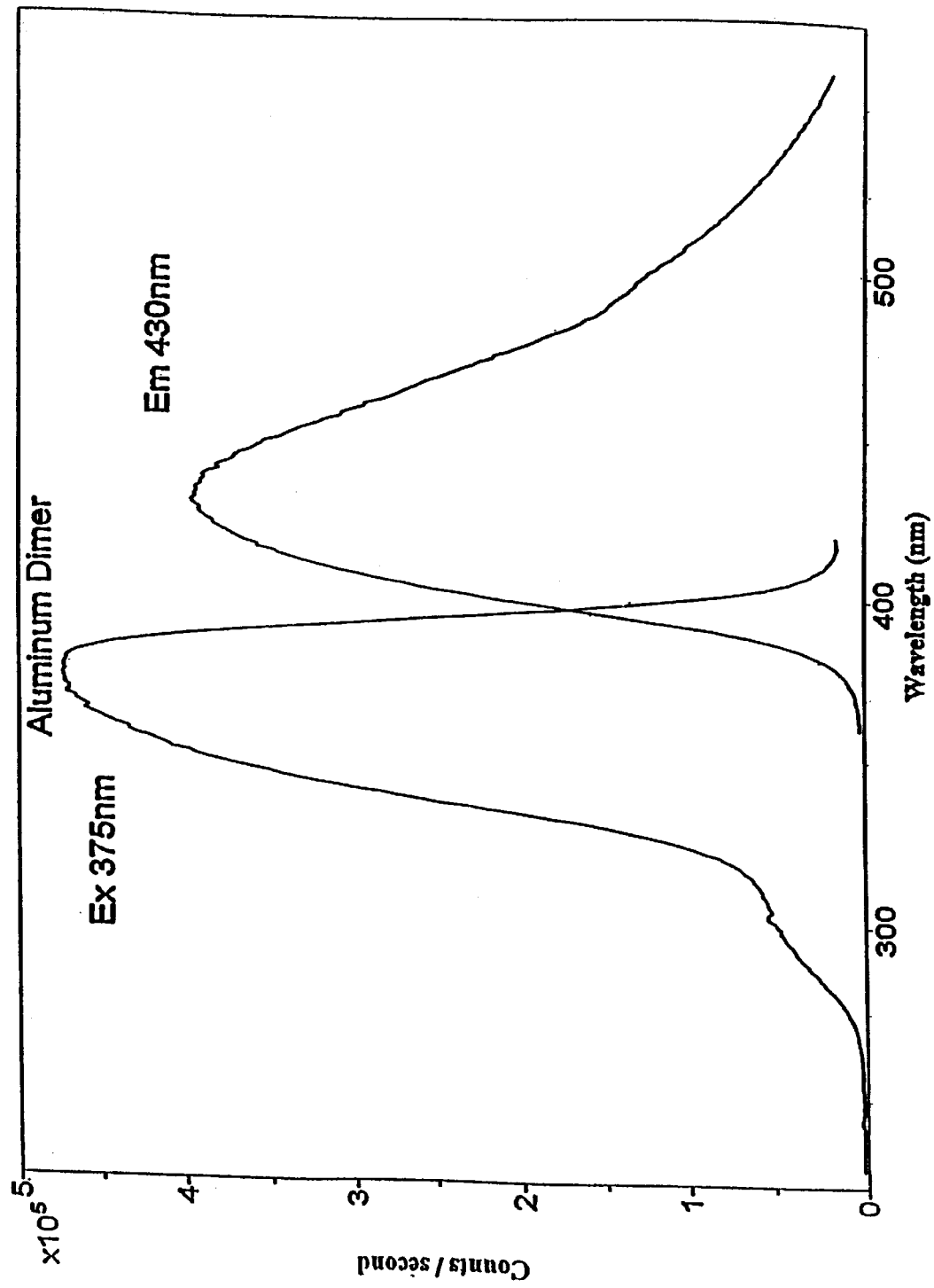
FIG. 10 shows the excitation and emission spectra of $Al_2(OCH(CF_3)_2)_3(azain)_2(CH_3)$.
Figure 11:
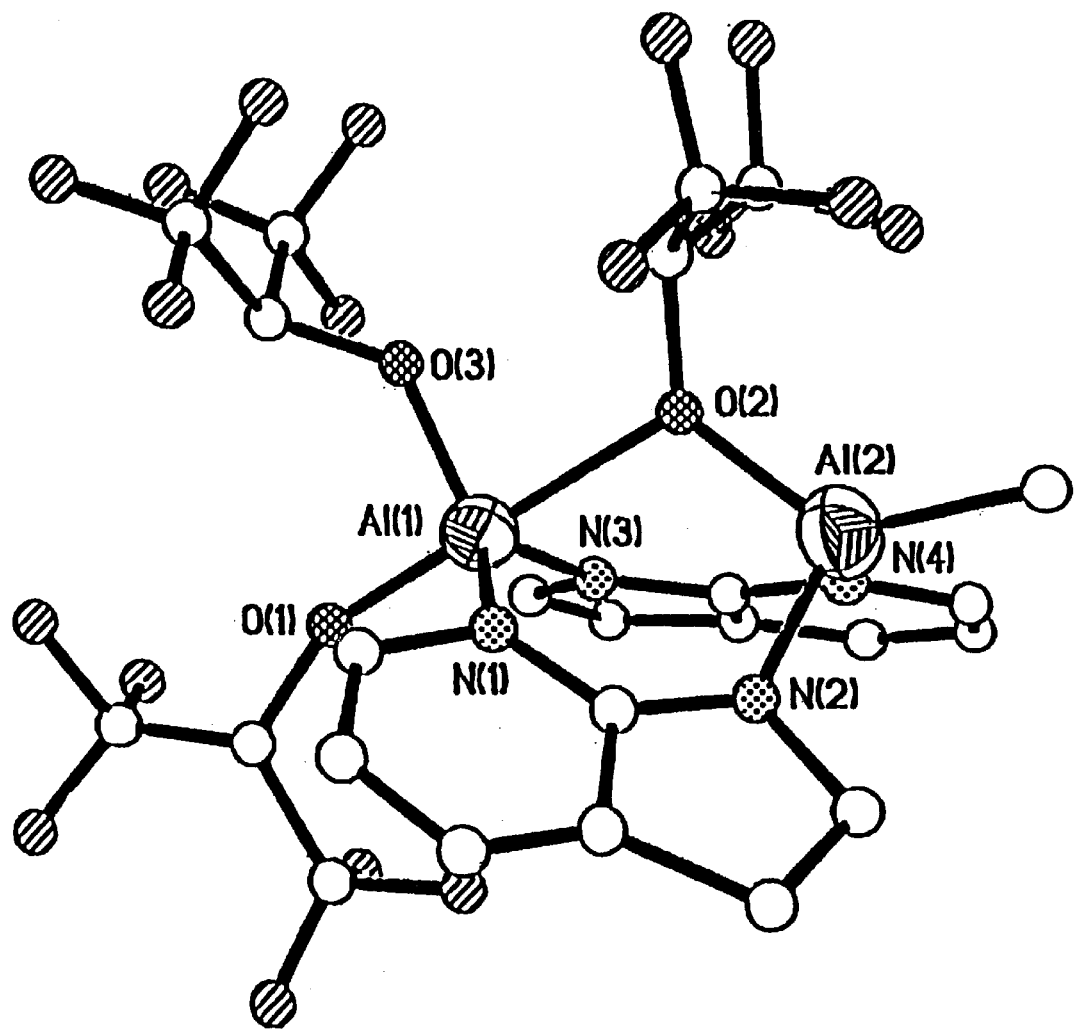
FIG. 11 shows the crystal structure of $Al_2(OCH(CF_3)_2)_3(azain)_2(CH_3)$.

Compound $Al_2(OCH(CF_3)_2)_3(azain)_2(CH_3)$ is an example of stable aluminum complexes where the reactive methyl groups are replaced by alkoxy groups. $Al_2(OCH(CF_3)_2)_3(azain)_2(CH_3)$ was obtained by the following procedure: 200 mg (1.70 mmol) of 7-azaindole in 8 mL of toluene was reacted with 847 mL (1.70 mmol) of $Al(CH_3)_3$ (2.0 M in hexane) at 23° C. under nitrogen for 1 h. 386 mg (2.30 mmol) of hexafluoro-2-propanol in 2 mL of toluene was added to the reaction mixture. This mixture was stirred for additional 3 h at 23° C. The volume of the solution was then concentrated to about 2 mL by vacuum. After several days standing at 23° C., colorless crystals of $Al_2(OCH(CF_3)_2)_3(azain)_2(CH_3)$ were obtained in 65% yield. Compound $Al_2(OCH(CF_3)_2)_3(azain)_2(CH_3)$ has a blue emission band at $\lambda_{max}$=430 nm (FIG. 10). Its structure was determined by single-crystal X-ray diffraction analysis. $Al_2(OCH(CF_3)_2)3(azain)_2(CH_3)$ contains two chemically non-equivalent aluminum environments. One of the aluminum atoms is coordinated by two hexafluoro-2-propanolato ligands and the other is coordinated by a methyl ligand. There is a bridging hexafluoro-2-propanolato ligand and two bridging 7-azaindole ligands in the molecule (FIG. 11).

Example 9

Synthesis of $Al_3(OCH(CF_3)_2)_2(O)(azain)_4(CH_3)$

Figure 12:
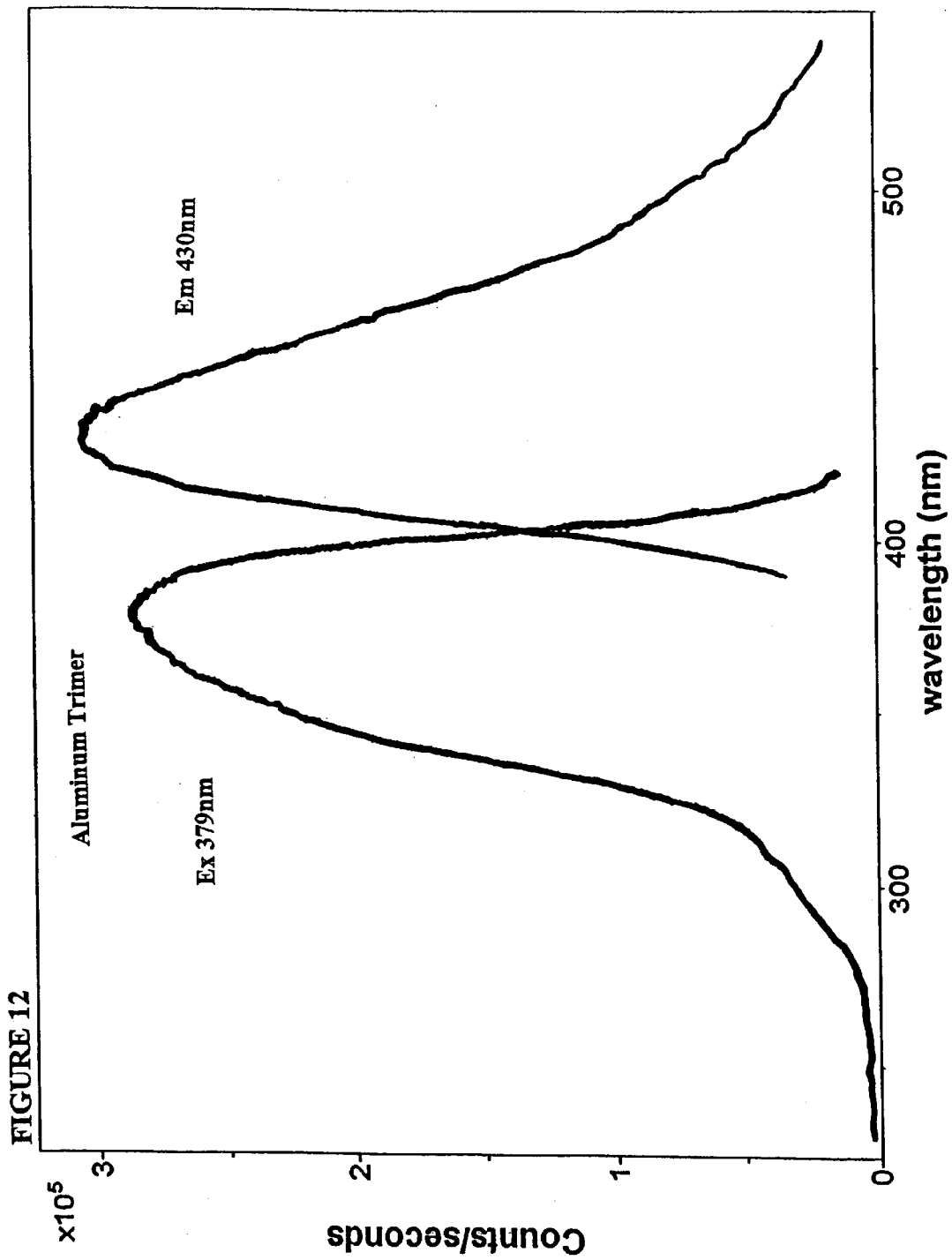
FIG. 12 shows the excitation and emission spectra of $Al_3(OCH(CF_3)_2)_2(O)(azain)_4(CH_3)$.
Figure 13:
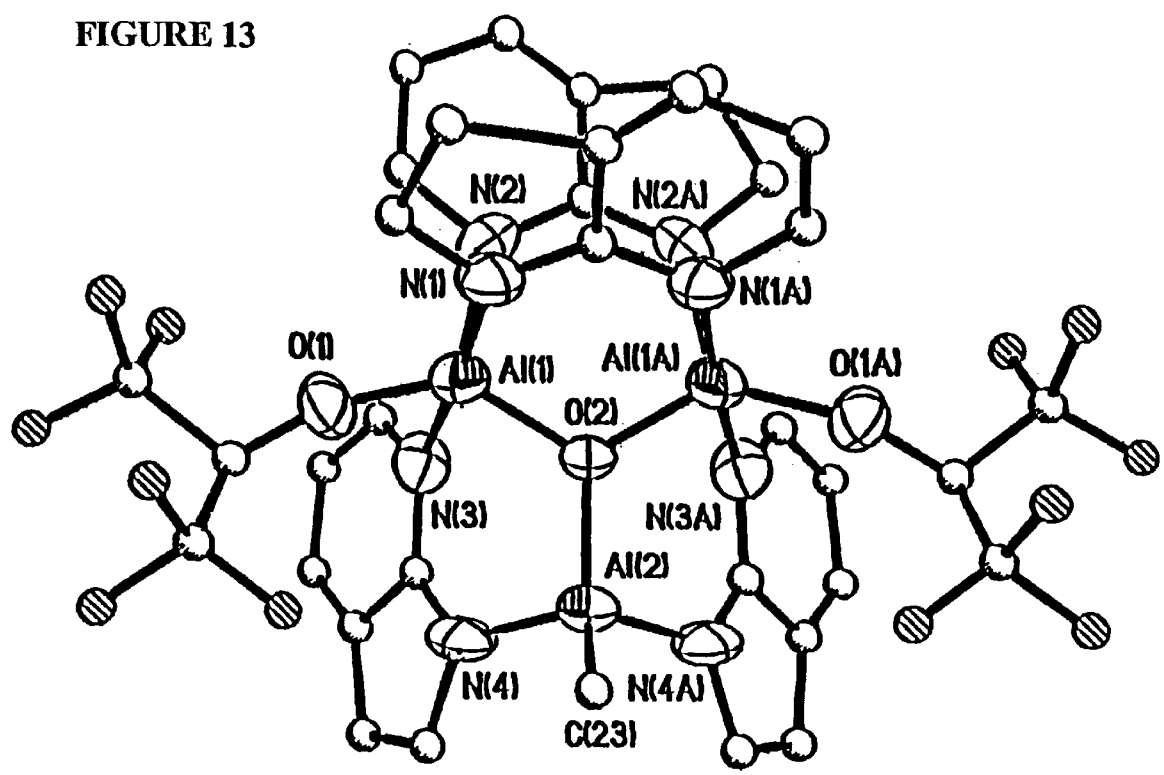
FIG. 13 shows the crystal structure of $Al_3(OCH(CF_3)_2)_2(O)(azain)_4(CH_3)$.

Compound $Al_3(OCH(CF_3)_2)_2(O)(azain)_4(CH_3)$ is the second example of alkoxy or oxo ligand-stabilized aluminum compounds. It was obtained by the following procedure: 200 mg (1.70 mmol) of 7-azaindole in 7 mL of toluene was reacted with 423 mL (0.846 mmol) of $Al(CH_3)_3$ (2.0 M in hexane) at 23° C. under nitrogen for 3 h. 142 mg of hexafluoro-2-propanol (0.846 mmol) in 3 mL of toluene was added. The mixture was stirred for another 3 h and concentrated to about 2 mL by vacuum. 2 mL of THF and 1 mL of hexane were added to the solution to crystallize the product. After two days, colorless crystals of $Al_3(OCH(CF_3)_2)_2(O)(azain)_4(CH_3)$ were obtained in 62% yield. Compound $Al_3(OCH(CF_3)_2)_2(O)(azain)_4(CH_3)$ has a blue emission band at $\lambda_{max}$=430 nm (FIG. 12). Its crystal structure was determined by X-ray diffraction analysis. $Al_3(OCH(CF_3)_2)_2(O)(azain)_4(CH_3)$ has three aluminum ions linked by a triply bridging oxygen atom. There are four bridging 7-azaindole ligands in the molecule. The two alkoxy ligands function as monodentate ligands (FIG. 13).

Example 10

Synthesis of $B(C_2H_5)_2(azain)(azainH)$

Figure 14:
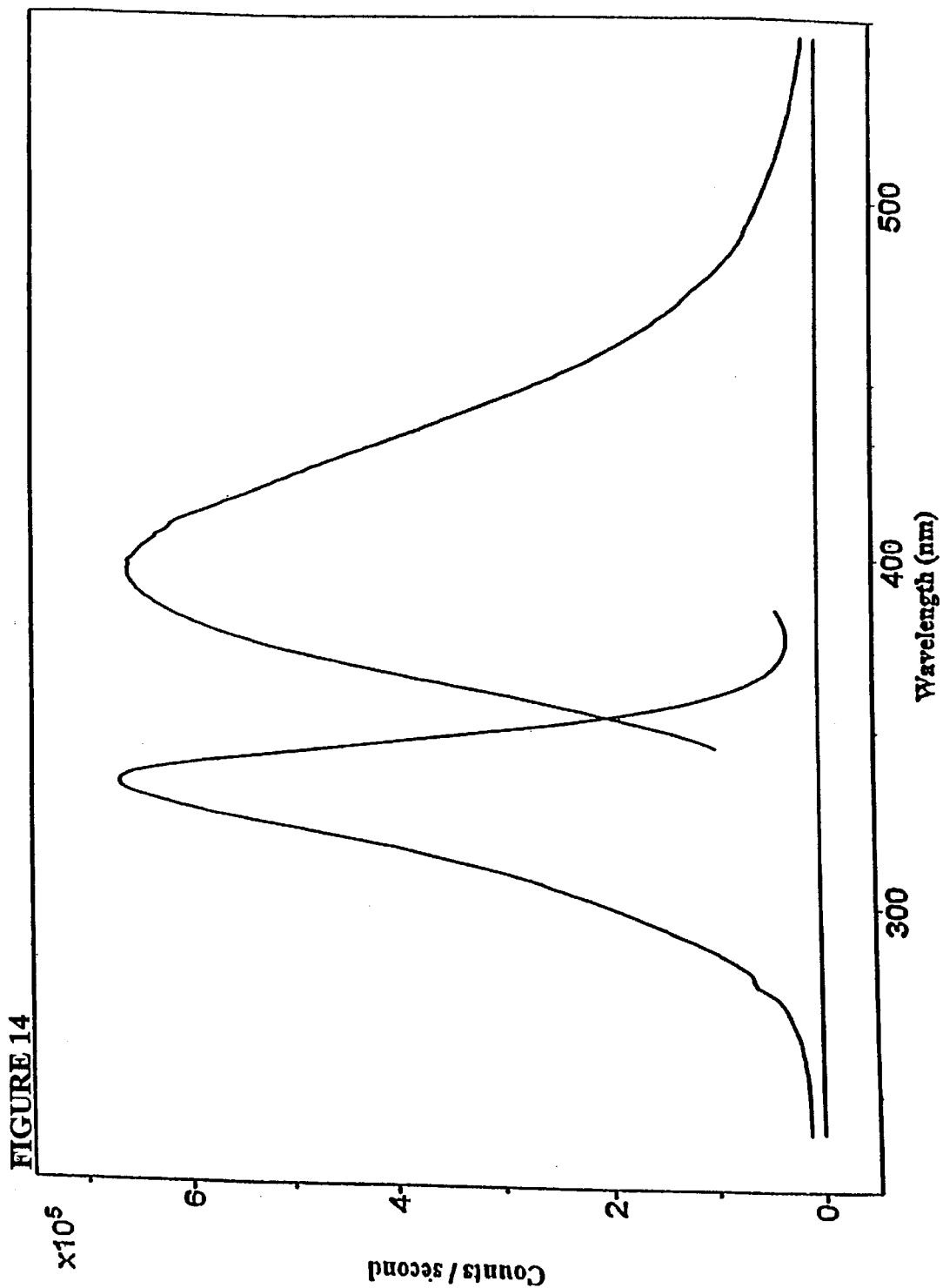
FIG. 14 shows the excitation and emission spectra of $B(C_2H_5)_2(azain)(azainH)$.
Figure 15:
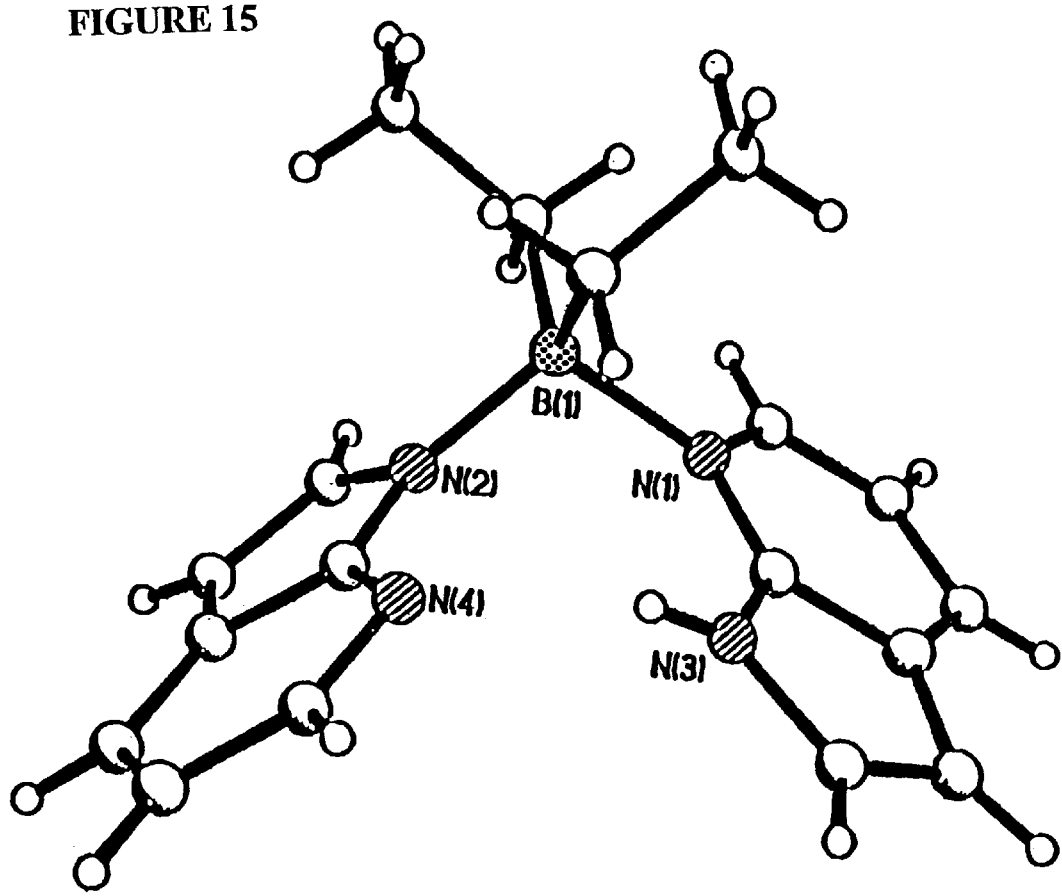
FIG. 15 shows the crystal structure of $B(C_2H_5)_2(azain)(azainH)$.

Blue luminescent compound $B(C_2H_5)_2(azain)(azainH)$ was made according to the following procedure: 200 mg (1.70 mmol) of 7-azaindole in 7 mL toluene was reacted with 1.70 mL (1.70 mmol) of $B(C_2H_5)_3$ (1.0 M in hexane) under nitrogen. This mixture was refluxed for 4 h under nitrogen. After the concentration of the solution, colorless crystals of $B(C_2H_5)_2(azain)(azainH)$ were obtained in 46% yield. Compound $B(C_2H_5)_2(azain)(azainH)$ has a blue emission band at $\lambda_{max}$=397 nm (FIG. 14). Its crystal structure has been determined by X-ray diffraction analysis. Two 7-azaindole ligands, a neutral one and a deprotonated one, are bound to the boron center (FIG. 15).

Example 11

Synthesis of $B_2(C_2H_5)_2(azain)_2(O)$

Figure 16:
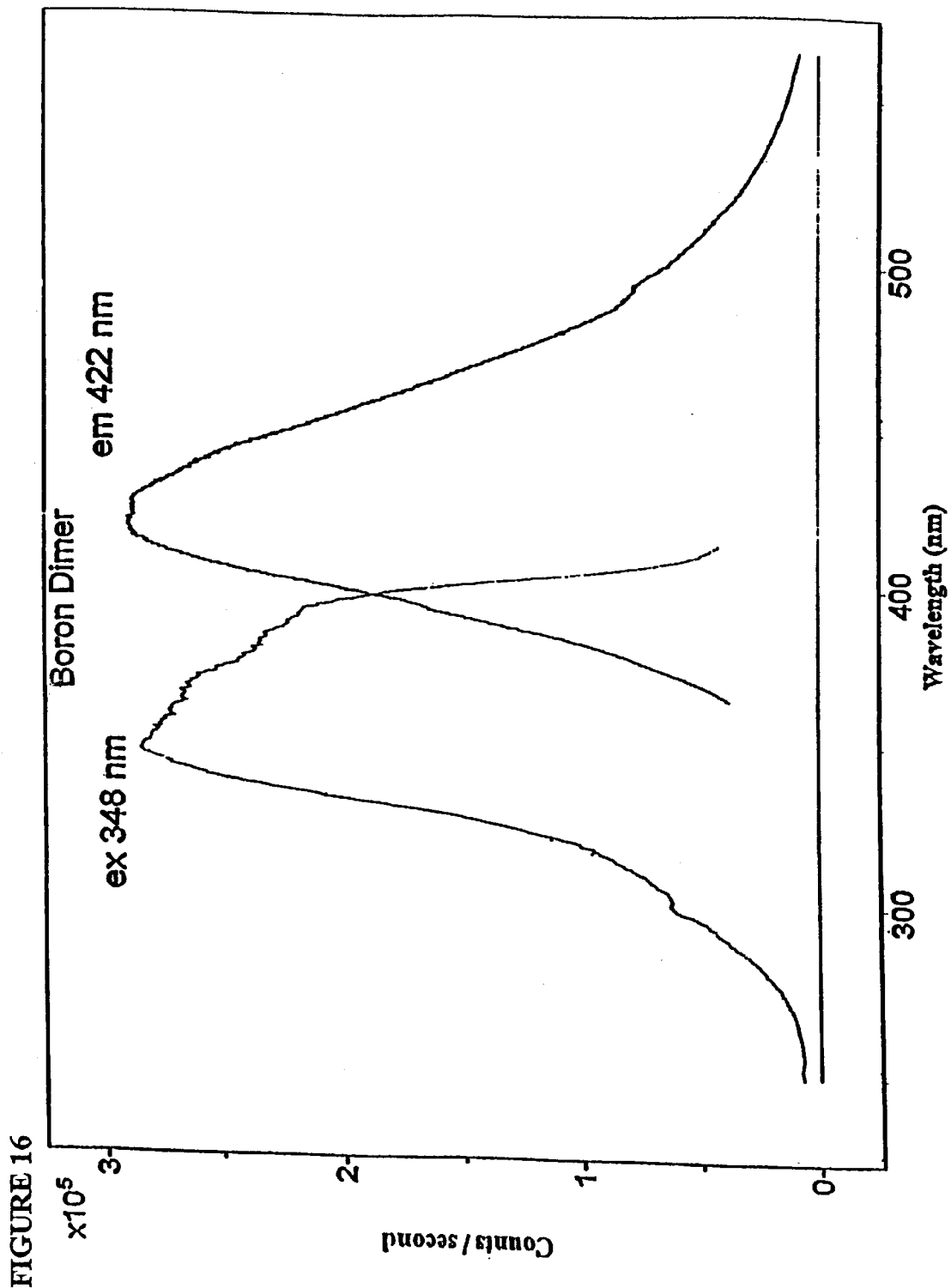
FIG. 16 shows the excitation and emission spectra of $B_2(C_2H_5)_2(azain)_2O$.
Figure 17:
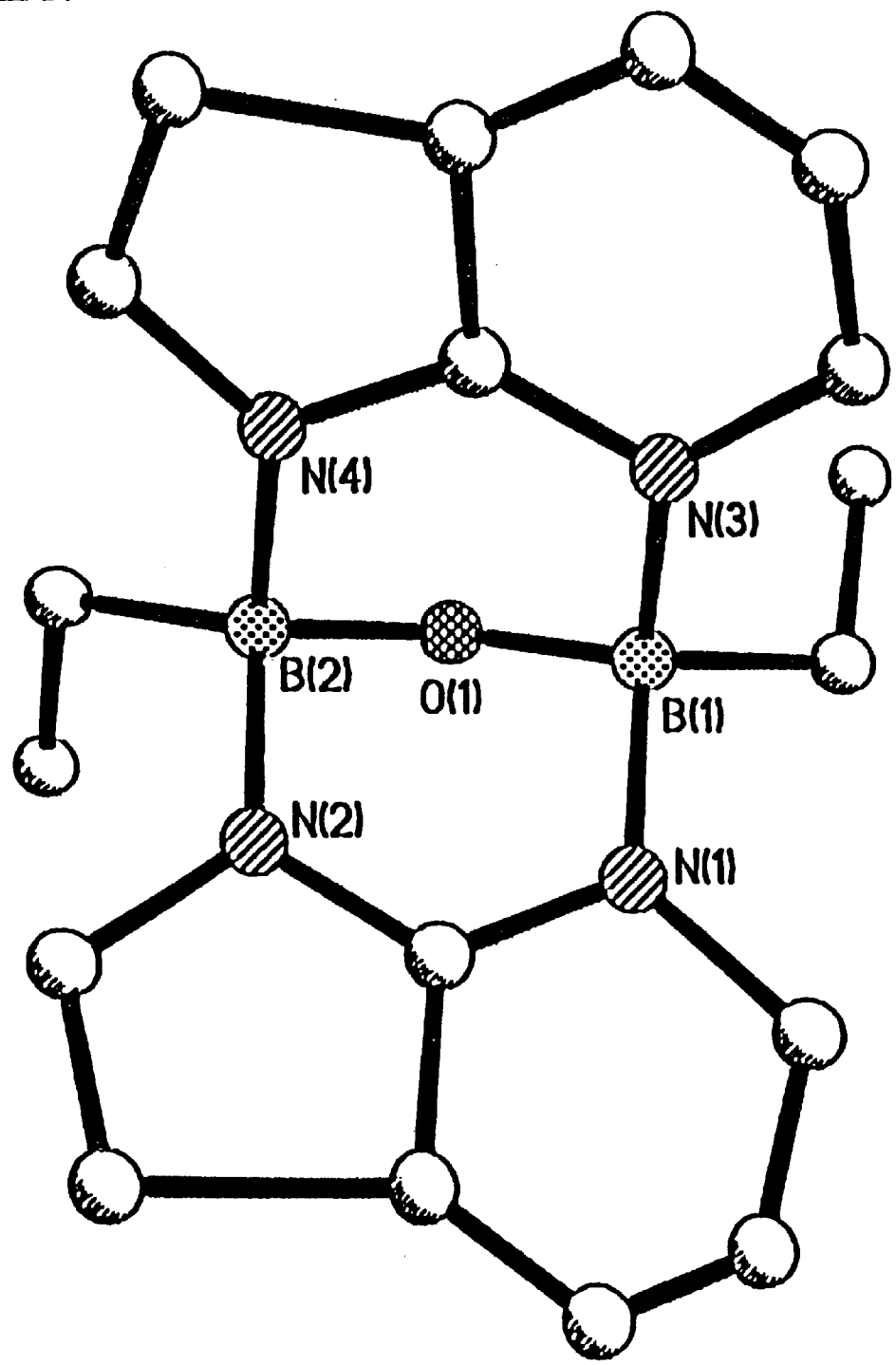
FIG. 17 shows the crystal structure of $B_2(C_2H_5)_2(azain)_2O$.

Compound $B_2(C_2H_5)_2(azain)_2(O)$ has been demonstrated to be a stable blue luminescent boron compound. This compound was obtained by the following procedure: 500 mg (4.23 mmol) of 7-azaindole in 20 mL of toluene was reacted with 4.23 mL (4.23 mmol) of $B(C_2H_5)_3$ (1.0 M in hexane) under nitrogen at 23° C. After the mixture was stirred for 3 h, 3 drops of water were added to the solution via a pipette. The reaction mixture was stirred for another 4 h. It was then concentrated to a volume of 3 mL. 2 mL of hexane was added to crystallize the product. Colorless crystals of $B_2(C_2H_5)_2(azain)_2(O)$ formed after about 24 h at 23° C. Compound $B_2(C_2H_5)_2(azain)_2(O)$ has a blue emission band at $\lambda_{max}$=422 nm (FIG. 16). Both blue photoluminescence and blue electroluminescence have been demonstrated. The structure of $B_2(C_2H_5)_2(azain)_2(O)$ was determined by X-ray diffraction analysis. It contains two boron atoms linked by an oxygen atom. The two boron centers are also bound by two 7-azaindole ligands (FIG. 17). This compound is remarkably stable towards air and moisture. It melts at 290°

Example 12

Synthesis of 2-phenyl-7-azaindole

The synthetic procedure of R. Herbert and D. G. Wibberley, *J. Chemical Society*, C, 1505 (1969), was employed, with minor modifications.

Figure 18:
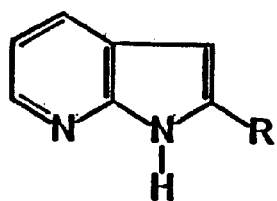
FIG. 18 shows the structure of 2-substituted 7-azaindole.

2-phenyl-7-azaindole was prepared in two steps. First, 2-amino-3-picoline was reacted with benzoyl chloride in chloroform in the presence of pyridine to produce 2-benzamido-3-picoline in 33% yield. Second, pyrolysis of 2-benzamido-3-picoline in N-methylaniline in the presence of NaH at 280° C. was performed to produce 2-phenyl-7-azaindole (FIG. 18) in 58% yield. This compound was characterized by NMR spectroscopy.

Example 13

Synthesis of 2-methyl-7-azaindole

The synthetic procedure of R. Herbert and D. G. Wibberley, *J. Chemical Society*, C, 1505 (1969), was employed, with minor modifications.

2-methyl-7-azaindole was prepared in two steps. First, 2-amino-3-picoline was reacted with acetyl chloride in toluene in the presence of pyridine to produce 2-acetamido-3-picoline in 65% yield. Second, pyrolysis of 2-acetamido-3-picoline in N-methylaniline in the presence of NaH at 280° C. was performed to produce 2-methyl-7-azaindole (FIG. 18) in 23% yield. This compound was characterized by NMR spectroscopy.

Example 14

Synthesis of $Al_3(CH_3)_3(O)(Ph\text{-azain})_4$

Figure 19:
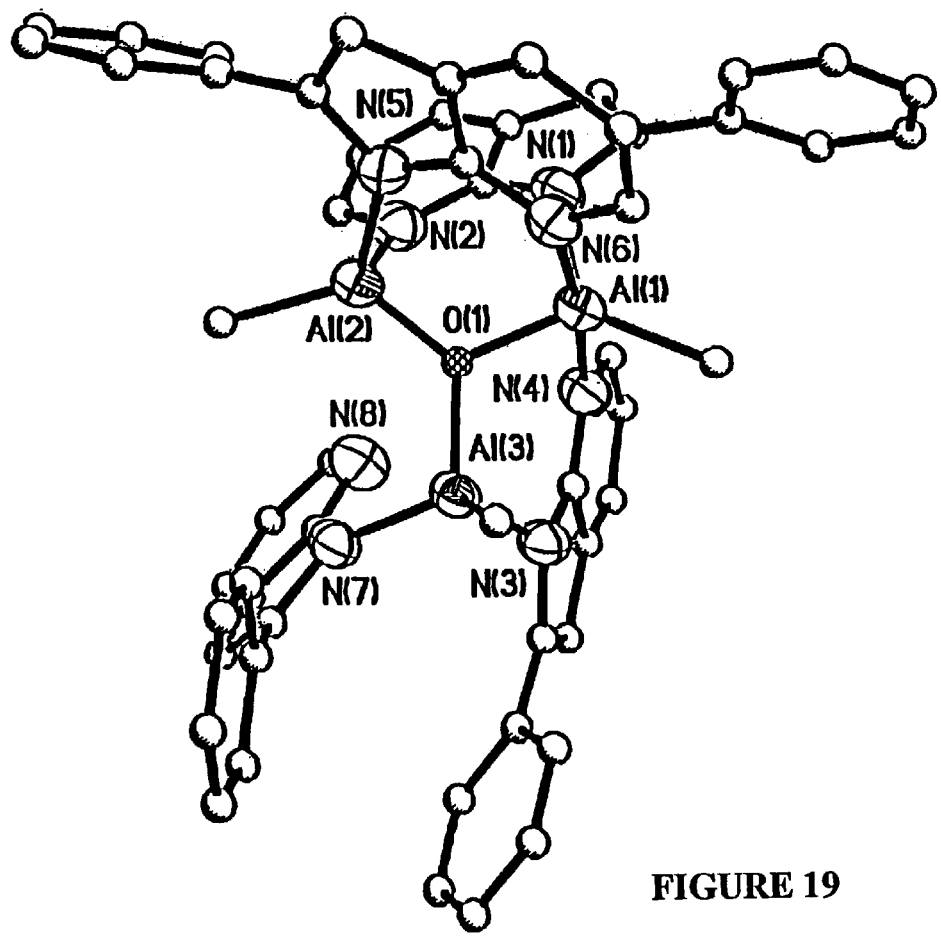
FIG. 19 shows the crystal structure of $Al_3(CH_3)_3(O)(Ph\text{-}azain)_4$.
Figure 20:
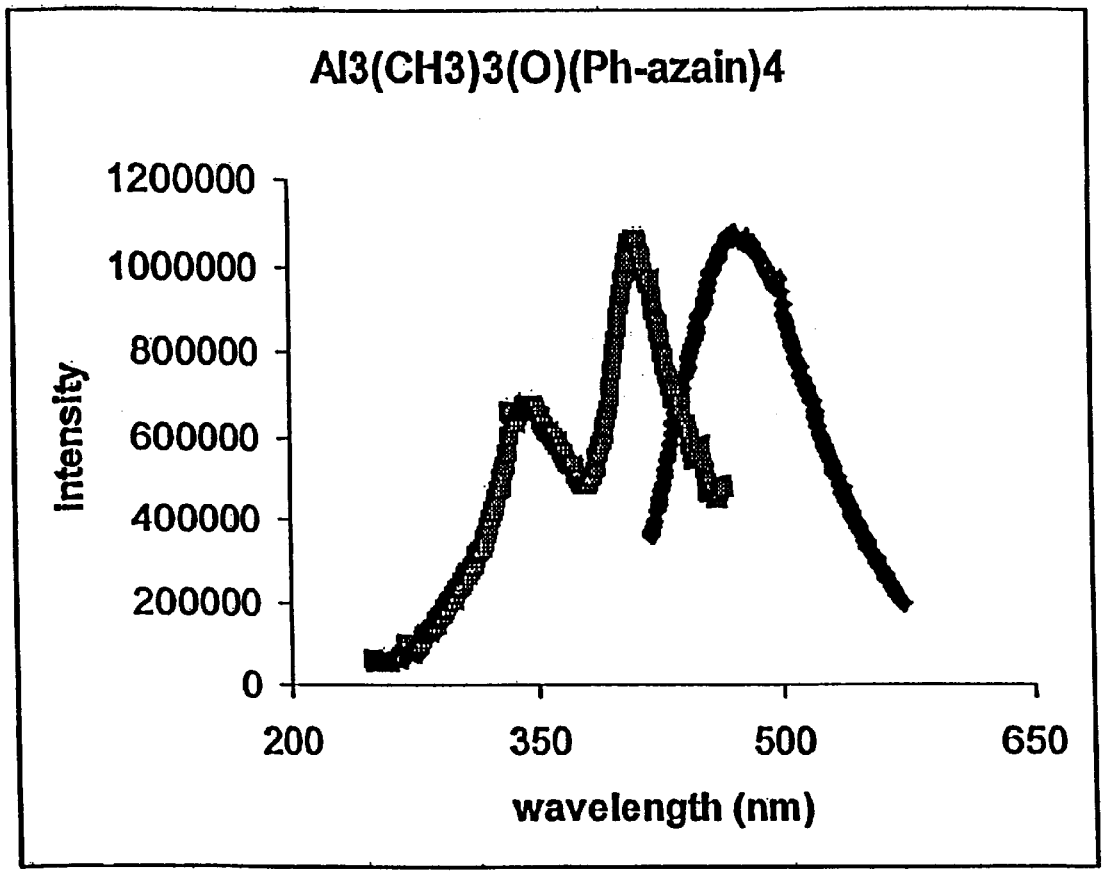
FIG. 20 shows the excitation and emission spectra of $Al_3(CH_3)_3(O)(Ph\text{-}azain)_4$.

2-Phenyl-7-azaindole (0.078 g, 0.40 mmol) in 10 mL toluene was heated to 60° C. After all of the 2-phenyl-7-azaindole was dissolved in the toluene, $Al(CH_3)_3$ (0.15 mL, 2M, 0.3 mmol) was added. The solution was stirred for 5 h at room temperature while water-saturated $N_2(g)$ was passed through the reaction container. The solution was stirred for another 15 h. The mixture was concentrated to about 2 mL by vacuum. Colorless crystals of $Al_3(CH_3)_3(O)(Ph\text{-azain})_4$ (FIG. 19) were obtained. Yield: 0.140 g (77%). This compound has an emission maximum at $\lambda=472$ nm and an excitation maximum, $\lambda=375$ nm (FIG. 20).

Example 15

Synthesis of $Al_3(CH_3)_3(O)(CH_3\text{-azain})_4$

Figure 21:
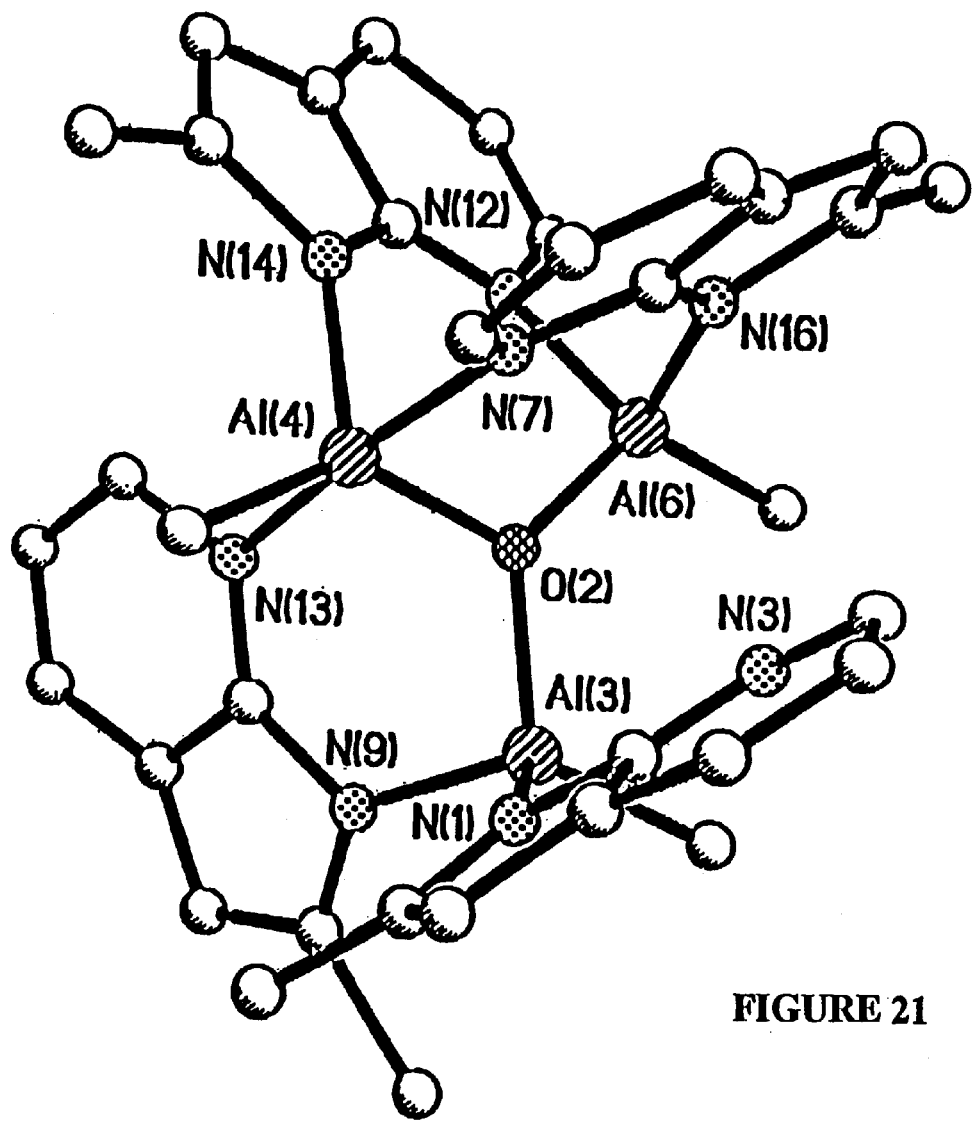
FIG. 21 shows the crystal structure of $Al_3(CH_3)_3(O)(CH_3\text{-}azain)_4$.
Figure 22:
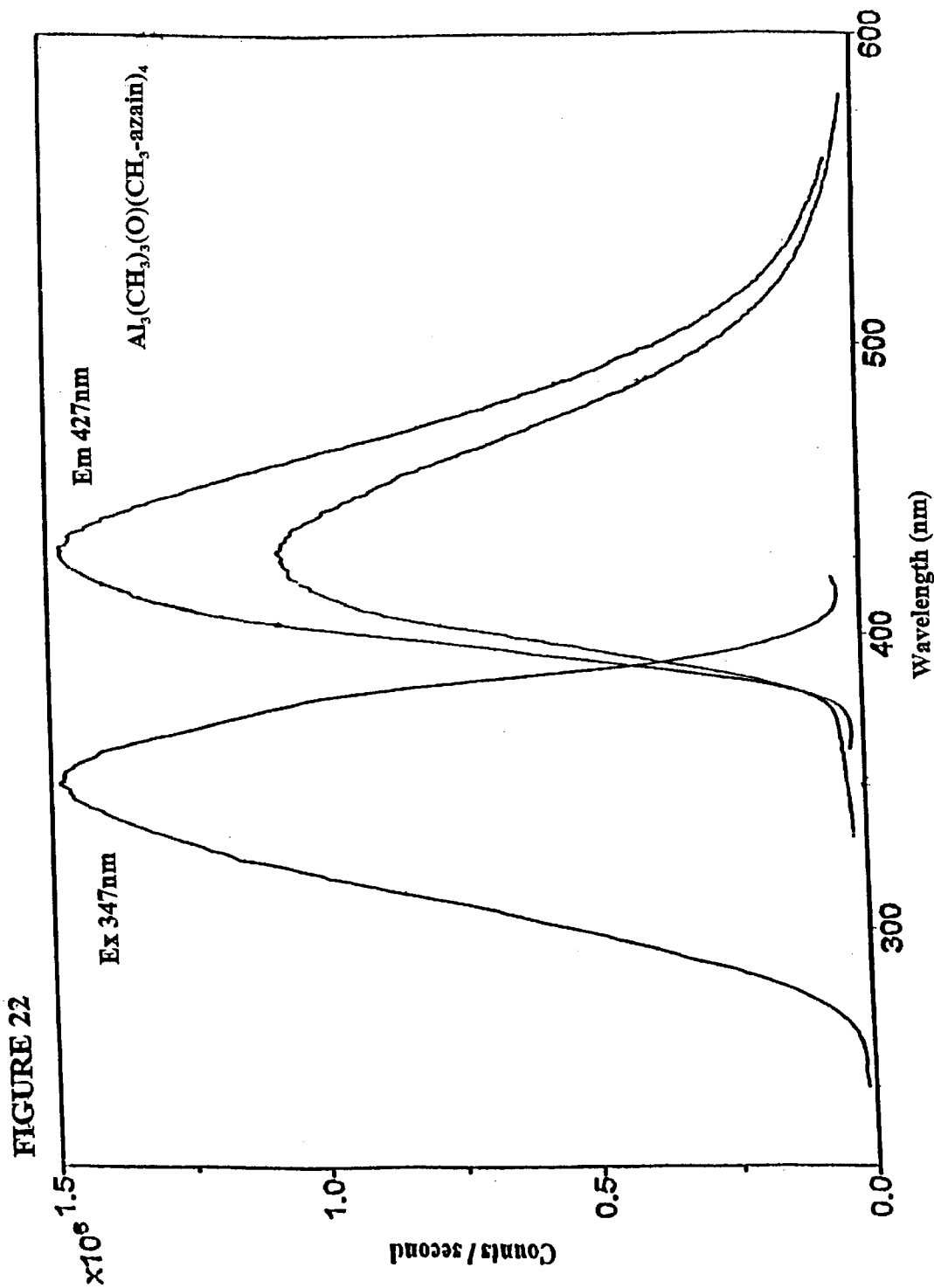
FIG. 22 shows the excitation and emission spectra of $Al_3(CH_3)_3(O)(CH_3\text{-}azain)_4$.

2-Methyl-7-azaindole (0.159 g, 1.20 mmol) in 8.0 mL of toluene was reacted with $Al_3(CH_3)_3$ (0.45 mL, 2M, 0.90 mmol) and the solution was stirred for 5 h at room temperature. Water-saturated nitrogen gas was passed through the reaction container. After the solution was stirred for another 15 h, it was concentrated to about 2 mL by vacuum. Colorless crystals of $Al_3(CH_3)_3(O)(CH_3\text{-azain})_4$ (FIG. 21) were obtained. Yield: 0.142 g (71%). This compound has an emission maximum at $\lambda$425 nm (FIG. 22).

Example 16

Synthesis of pentafluorophenyl-2-pyridylamine

This compound was synthesized according to the method of R. Koppang, *J. Organometallic Chemistry*, 46, 193 (1972). Lithium (2-pyridyl)amide was obtained from the reaction of lithium amide with 2-aminopyridine in a 1:1 ratio in THF. The reaction of lithium (2-pyridyl)amide with hexafluorobenzene in THF at 0° C. yielded pentafluorophenyl-2-pyridylamine (PFPA-H; 2-pentafluoroanilinopyridine) (FIG. 23) in 76% yield. The product was characterized by NMR spectroscopy.

Example 17

Synthesis of $Al(PFPA)_3$

Figure 24:
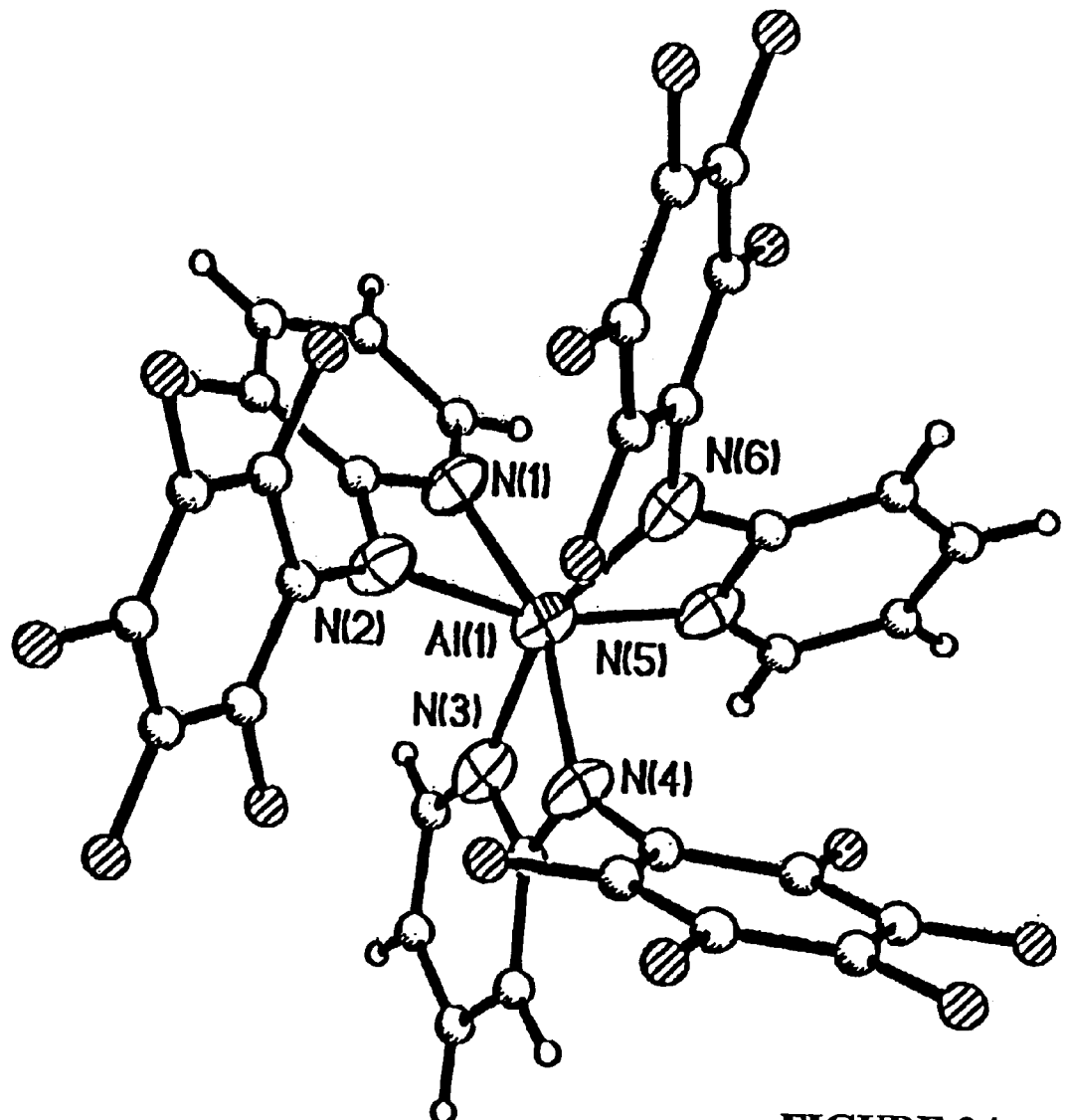
FIG. 24 shows the crystal structure of $Al(PFPA)_3$.
Figure 25:
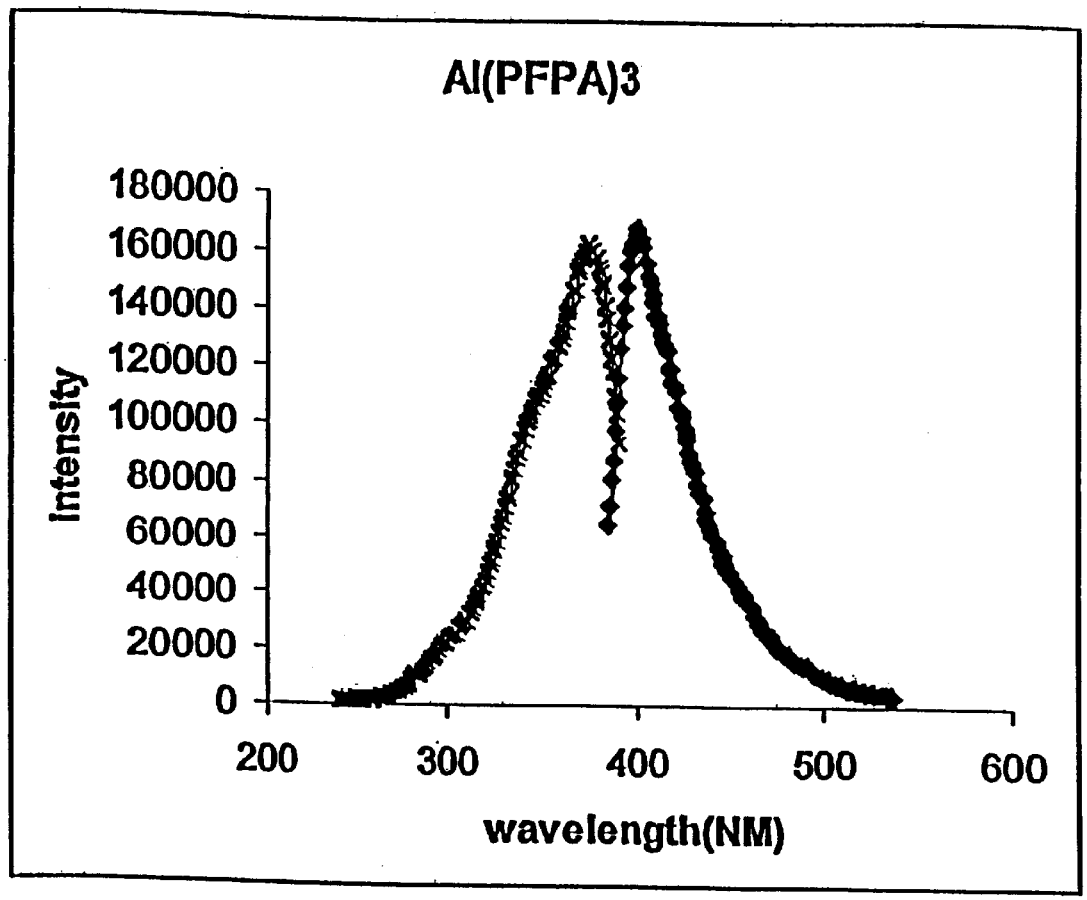
FIG. 25 shows the excitation and emission spectra of $Al(PFPA)_3$.

Pentafluorophenyl-2-pyridylamine (0.156 g, 0.60 mmol) in 5 mL of toluene was reacted with $Al(CH_3)_3$ (0.10 mL 2.0 M in hexane, 0.20 mmol) at room temperature under nitrogen for 12 h. The mixture was concentrated to about 1 mL by vacuum. Colorless crystals of $Al(PFPA)_3$ (FIG. 24) were obtained. Yield: 0.126 g (78%). This compound has an emission maximum at $\lambda$401 nm when excited at $\lambda$344 nm (FIG. 25).

Example 18

Synthesis of $B(Ph)_3(azainH)$

Figure 26:
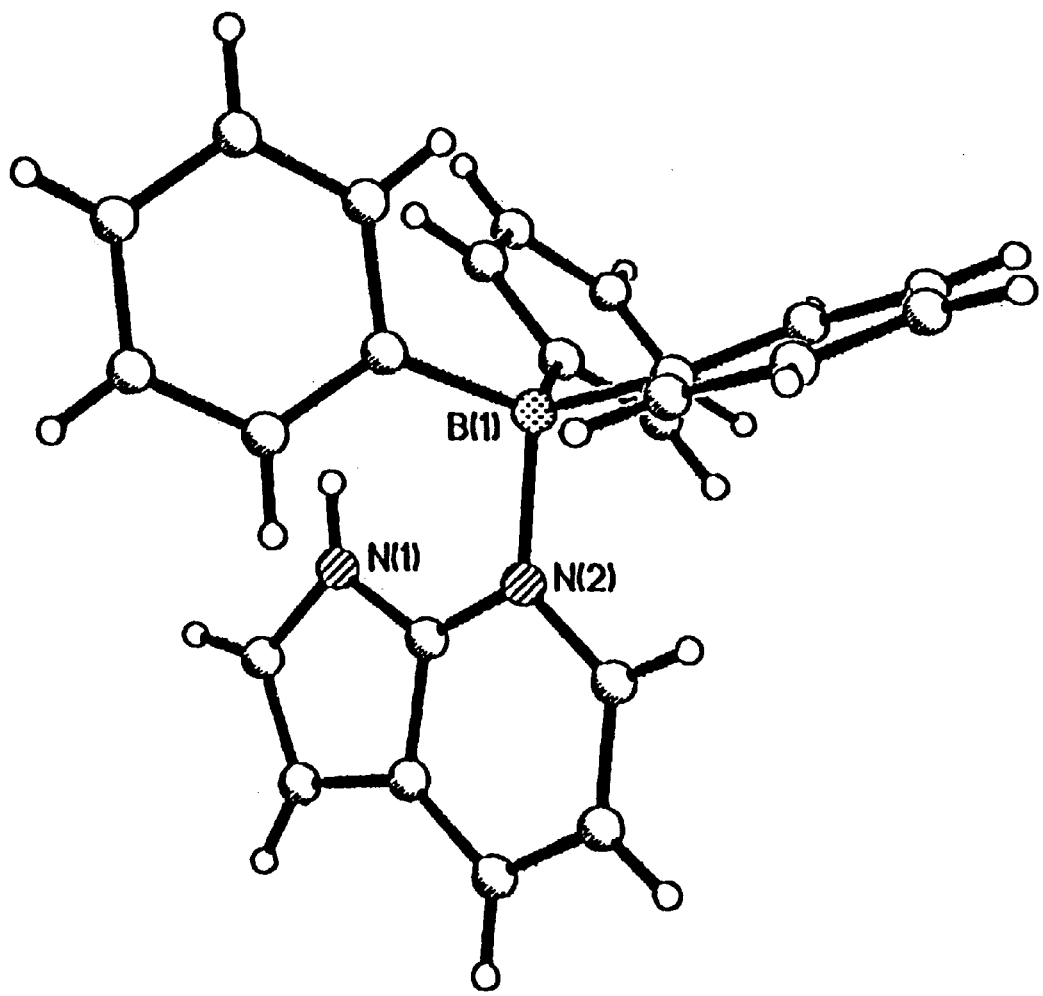
FIG. 26 shows the crystal structure of $BPh_3(azainH)$.
Figure 27:
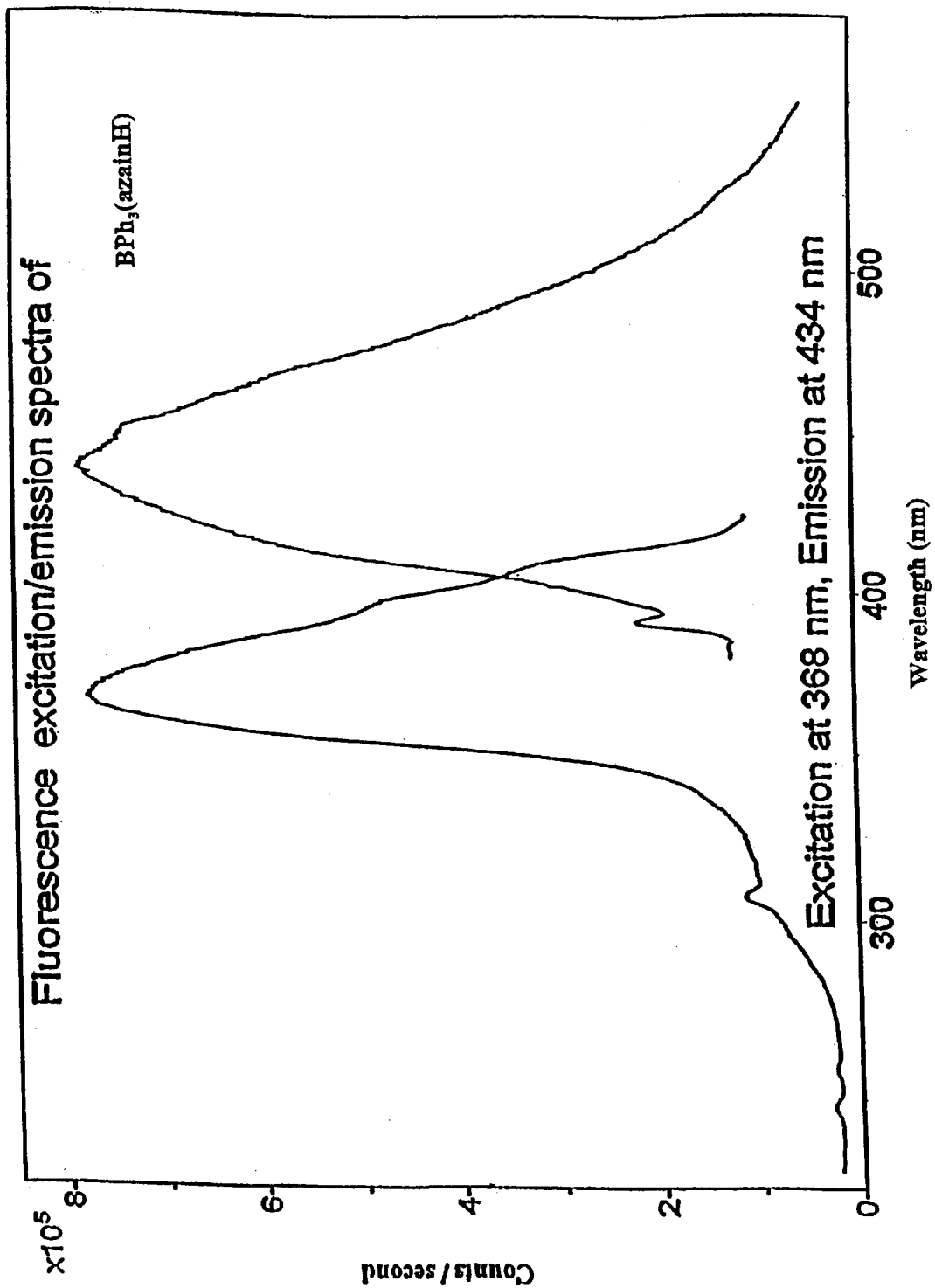
FIG. 27 shows the excitation and emission spectra of $BPh_3(azainH)$.

Triphenylborane (1.211 g, 5 mmol) in 20 mL toluene was reacted with 7azaindole (0.592 g, 5 mmol) for 5 h. The solvent was removed by vacuum. The solid was transferred to a drybox and re-dissolved in a minimum volume of $CH_2Cl_2$. After the addition of 2–3 mL of hexane, colorless crystals of $B(Ph)_3(azainH)$ (FIG. 26) were obtained. Yield: 1.18 g (65%). This compound has an emission maximum at a $\lambda=434$ nm (FIG. 27).

Example 19

Synthesis of $B(OPh)_3(azainH)$

Figure 28:
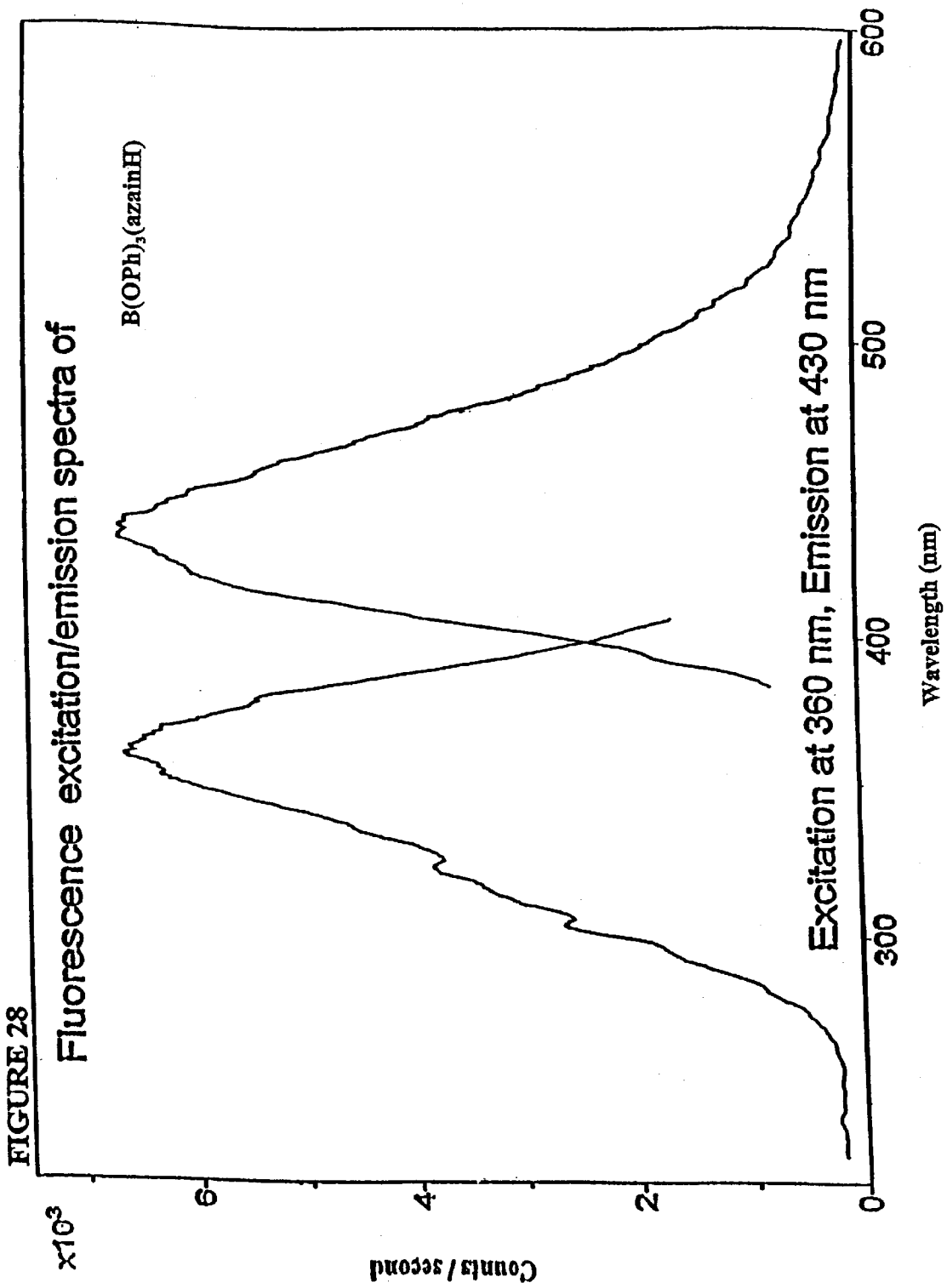
FIG. 28 shows the excitation and emission spectra of B(OPh)$_3$(azain)

Triphenylborate (0.870 g, 3 mmol) in 20 mL toluene was reacted with 7-azaindole (0.354 g, 3 mmol) for 5 h. The solvent was removed by vacuum. The solid was transferred to a drybox and re-dissolved in a minimum volume of $CH_2Cl_2$. After the addition of 2 mL hexane, colorless crystals of $B(OPh)_3(azainH)$ were obtained. Yield: 0.865 g (71%). This compound has an analogous crystal structure to that of $B(Ph)_3(azainH)$ shown in FIG. 26, and has an emission maximum at $\lambda=430$ nm (FIG. 28).

Although this invention is described in detail with reference to preferred embodiments thereof, these embodiments are offered to illustrate but not to limit the invention. It is possible to make other embodiments that employ the principles of the invention and that fall within its spirit and scope as defined by the claims appended hereto.

What is claimed is:

1. A photoluminescent or electroluminescent compound having a formula selected from the group consisting of:
   (i) $[AlR_2(azain)]_n$, where n is 1 or 2,
   (ii) $[Al_2R_3(O)(dpa)]_n$, where n is 2,
   (iii) $[Al_2R_3(O)(azain)]_n$, where n is 2,
   (iv) $Al(PFPA)_3$, and
   (v) derivatives of (i), (ii), (iii), and (iv) where azain or dpa is substituted on one or more atoms with an aliphatic, aromatic, alkoxy, hydroxyl, halogen, amino, nitro, or nitrile group, or $-CF_3$, and/or where azain or dpa is modified to include an ether, epoxide, ester or amide functionality,
   where R is aliphatic, aryl or alkoxyl, azain is deprotonated 7-azaindole, dpa is deprotonated di-2-pyridyl amine, and PFPA is deprotonated pentafluorophenyl-2-pyridylamine.

2. A method of synthesizing a compound as claimed in claim 1, comprising a step selected from the group consisting of:

$$n\ AlR_3 + n\ azainH \rightarrow [AlR_2(azain)]_n + n\ RH,$$

where n=1 or 2;

$$2n\ AlR_3 + n\ H_2O + n\ dpaH\ (or\ azainH) \rightarrow [Al_2R_3(O)(dpa)]_n$$

or $$[Al_2R_3(O)(azain)]_n + 3n\ RH,$$

where n=2; and $$AlR_3 + 3PFPA-H \rightarrow Al(PFPA)_3 + 3RH.$$

3. A photoluminescent or electroluminescent compound having a formula selected from the group consisting of:
(i) $Al_2R_2(azain)_4$,
(ii) $Al_2(R)(azain)_2(OR')_3$,
(iii) $Al_3(R)(azain)_4(OR')_2(O)$,
(iv) $Al_3R_3(azain)_4(O)$, and
(v) derivatives of (i), (ii), (iii) and (iv) where azain is substituted on one or more atoms with an aliphatic, aromatic, alkoxy, hydroxyl, halogen, amino, nitro, or nitrile group, or —CF$_3$, and/or where azain is modified to include an ether, epoxide, ester or amide functionality,
where R and R' are aliphatic, aryl or alkoxyl, and azain is deprotonated 7-azaindole.

4. A method of synthesizing a compound as claimed in claim 3, comprising a step selected from the group consisting of:

$$2\ AlR_3 + 4\ azainH \rightarrow Al_2R_2(azain)_4 + 4RH,$$

$$2\ AlR_3 + 2\ azainH + 3\ R'OH\ Al_2(R)(azain)_2(OR')_3 + 5\ RH,$$

$$3\ AlR_3 + 4\ azainH + H_2O + 2\ R'OH \rightarrow Al_3(R)(azain)_4(OR')_2(O) + 8\ RH,$$

and $$3AlR_3 + 4\ azainH + H_2O \rightarrow Al_3(R)_3(azain)_4(O) + 6RH.$$

5. A photoluminescent or electroluminescent compound having a formula selected from the group consisting of:
(i) $[BR_2(azain)]_n$, where n is 1 or 2,
(ii) $B_2R_2(azain)_2(O)$,
(iii) $BR_3(azainH)$, and
(iv) derivatives of (i), (ii), and (iii) where azain is substituted on one or more atoms with an aliphatic, aromatic, alkoxy, hydroxyl, halogen, amino, nitro, or nitrile group, or —CF$_3$, and/or where azain is modified to include an ether, epoxide, ester or amide functionality,
where azain is deprotonated 7-azaindole and R is aliphatic, aryl or alkoxyl.

6. A method of synthesizing a compound as claimed in claim 5, comprising a step selected from the group consisting of:

$$n\ BR_3 + n\ azainH \rightarrow [BR_2(azain)]_n + n\ RH,$$

(n=1, 2), $$2\ BR_3 + 2\ azainH + H_2O \rightarrow B_2R_2(azain)_2(O) + 4\ RH,$$

and $$BR_3 + azainH \rightarrow BR_3(azainH).$$

7. A photoluminescent or electroluminescent compound having a formula selected from the group consisting of:
(i) $[BR(dpa)_2]_n$, and
(ii) derivatives of (i), where dpa is substituted on one or more atoms with an aliphatic, aromatic, alkoxy, hydroxyl, halogen, amino, nitro, or nitrile group, or —CF$_3$, and/or where dpa is modified to include an ether, epoxide, ester or amide functionality,
where n is 1, dpa is deprotonated di-2-pyridyl amine, and R is aliphatic, aryl or alkoxyl.

8. A method of synthesizing a compound as claimed in claim 7, comprising a step:

$$n\ BR_3 + 2n\ dpaH \rightarrow [BR(dpa)_2]_n + 2n\ RH,$$

where n is 1.

9. A composition comprising a compound as claimed in claim 1, 3, 5, or 7 and an inert carrier.

10. A composition comprising a compound as claimed in claim 1, 3, 5, or 7, an organic polymer and a solvent.

11. A photoluminescent product or an electroluminescent product comprising a compound as claimed in claim 1, 3, 5, or 7.

12. The product of claim 11, wherein the product is a flat panel display device.

13. The product of claim 11, wherein the product is a luminescent probe.

14. A method of producing electroluminescence, comprising the steps of:
providing an electroluminescent compound as claimed in claim 1, 3, 5, or 7, and
applying a voltage across said compound so that said compound electroluminesces.

15. An electroluminescent device for use with an applied voltage, comprising:
a first electrode,
an emitter which is an electroluminescent compound as claimed in claim 1, 3, 5, or 7, and
a second, transparent electrode,
wherein voltage is applied to the two electrodes to produce an electric field across the emitter so that the emitter electroluminesces.

16. An electroluminescent device for use with an applied voltage, comprising:
a first electrode,
a second, transparent electrode,
an electron transport layer adjacent the first electrode,
a hole transport layer adjacent the second electrode, and
an emitter which is an electroluminescent compound as claimed in claim 1, 3, 5, or 7 interposed between the electron transport layer and the hole transport layer,
wherein voltage is applied to the two electrodes to produce an electric field across the emitter so that the emitter electroluminesces.

17. $[Al(CH_3)_2(azain)]_2$, where azain is deprotonated 7-azaindole.

18. $[Al(OR)_2(azain)]_2$, where R is aliphatic, aryl or alkoxyl, and azain is deprotonated 7-azaindole.

19. $[Al(OR)_2(dpa)]_2$, where R is aliphatic, aryl or alkoxyl, and dpa is deprotonated di-2-pyridyl amine.

20. $Al_2(CH_3)_6(O)_2(dpa)_2$, where dpa is deprotonated di-2-pyridyl amine.

21. $[Al(OPr^i)_2(azain)]_2$, where azain is deprotonated 7-azaindole, and $Pr^i$ is iso-propyl.

22. $B(dpa)X_2$, where dpa is deprotonated di-2-pyridyl amine, and X is halide or alkoxyl.

23. $Al_2(CH_3)_2(azain)_4$, where azain is deprotonated 7-azaindole.

24. $Al_2(OCH(CF_3)_2)_3(azain)_2(CH_3)$, where azain is deprotonated 7-azaindole.

25. $Al_3(OCH(CF_3)_2)_2(O)(azain)_4(CH_3)$, where azain is deprotonated 7-azaindole.

26. $B(C_2H_5)_2(azain)(azainH)$, where azain is deprotonated 7-azaindole.

27. $B_2(C_2H_5)_2(azain)_2(O)$, where azain is deprotonated 7-azaindole.

28. $Al(PFPA)_3$, where PFPA is deprotonated pentafluorophenyl-2-pyridylamine.

29. $Al_3(CH_3)_3(O)(Ph\text{-}azain)_4$, where Ph is phenyl and azain is deprotonated 7-azaindole.

30. $Al_3(CH_3)_3(O)(CH_3\text{-}azain)_4$, where azain is deprotonated 7-azaindole.

31. $B(Ph)_3(azainH)$, where Ph is phenyl and azain is deprotonated 7-azaindole.

32. $B(OPh)_3(azainH)$, where Ph is phenyl and azain is deprotonated 7-azaindole.

33. A method of producing electroluminescence, comprising the steps of:

providing an electroluminescent compound $Al(CH_3)_2(dpa)$, where dpa is deprotonated di-2-pyridyl amine, and applying a voltage across said compound so that said compound electroluminesces.

34. An electroluminescent device for use with an applied voltage, comprising:

a first electrode, an emitter which is an electroluminescent compound $Al(CH_3)_2(dpa)$, where dpa is deprotonated di-2-pyridyl amine, and a second, transparent electrode, wherein voltage is applied to the two electrodes to produce an electric field across the emitter so that the emitter electroluminesces.

35. An electroluminescent device for use with an applied voltage, comprising:

a first electrode, a second, transparent electrode, an electron transport layer adjacent the first electrode, a hole transport layer adjacent the second electrode, and an emitter which is an electroluminescent compound $Al(CH_3)_2(dpa)$, where dpa is deprotonated di-2-pyridyl amine, interposed between the electron transport layer and the hole transport layer, wherein voltage is applied to the two electrodes to produce an electric field across the emitter so that the emitter electroluminesces.

36. A method of producing electroluminescence, comprising the steps of:

providing an electroluminescent compound $BR_2(dpa)$, where dpa is deprotonated di-2-pyridyl amine and R is aliphatic or aryl, applying a voltage across said compound so that said compound electroluminesces.

37. An electroluminescent device for use with an applied voltage, comprising:

a first electrode, an emitter which is an electroluminescent compound $BR_2(dpa)$, where dpa is deprotonated di-2-pyridyl amine and R is aliphatic or aryl, and a second, transparent electrode, wherein voltage is applied to the two electrodes to produce an electric field across the emitter so that the emitter electroluminesces.

38. An electroluminescent device for use with an applied voltage, comprising:

a first electrode, a second, transparent electrode, an electron transport layer adjacent the first electrode, a hole transport layer adjacent the second electrode, and an emitter which is an electroluminescent compound $BR_2(dpa)$, where dpa is depronated di-2-pyridyl amine and R is aliphatic or aryl, interposed between the electron transport layer and the hole transport layer, wherein voltage is applied to the two electrodes to produce an electric field across the emitter so that the emitter electroluminesces.

* * * * *